(12) United States Patent
Kodali et al.

(10) Patent No.: US 6,291,409 B1
(45) Date of Patent: *Sep. 18, 2001

(54) PROCESS FOR MODIFYING UNSATURATED TRIACYLGLYCEROL OILS; RESULTING PRODUCTS AND USES THEREOF

(75) Inventors: Dharma R. Kodali, Plymouth; Keqiang Li, St. Paul, both of MN (US)

(73) Assignee: Cargill, Inc., Deephaven, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/342,388

(22) Filed: Jun. 29, 1999

Related U.S. Application Data

(63) Continuation-in-part of application No. 09/108,773, filed on Jul. 2, 1998, now Pat. No. 6,051,539.
(60) Provisional application No. 60/126,437, filed on Jan. 22, 1999, and provisional application No. 60/118,636, filed on Feb. 4, 1999.

(51) Int. Cl.[7] ...................... C10M 105/38; C10M 107/20
(52) U.S. Cl. ...................... 508/491; 508/485; 560/124; 554/24; 252/79
(58) Field of Search ............................................. 508/491

(56) References Cited

U.S. PATENT DOCUMENTS

| | | | |
|---|---|---|---|
| 4,472,313 | * | 9/1984 | Giger ..................................... 260/410 |
| 4,500,541 | * | 2/1985 | Hausberg et al. ..................... 514/466 |
| 5,229,023 | * | 7/1993 | Landis ................................... 560/127 |
| 5,427,704 | * | 6/1995 | Lawate ................................... 508/491 |
| 5,773,391 | * | 6/1998 | Lawate et al. ......................... 508/257 |
| 5,936,139 | * | 8/1999 | Schmid ................................... 800/281 |
| 6,051,539 | * | 4/2000 | Kodali et al. ......................... 508/491 |

FOREIGN PATENT DOCUMENTS

| | | |
|---|---|---|
| 0 712 834 A1 | 5/1996 | (EP) . |
| 1005641 | 9/1965 | (GB) . |
| 58-147498 | 9/1983 | (JP) . |

OTHER PUBLICATIONS

Deyrup, J. A. et al., "The Isomeric trans, trans–Bicyclo(6.1.0)non–4–enes," *Journal of Organic Chemistry*, vol. 40, No. 3, pp. 281–289 (Feb. 7, 1975).

Gensler W. J. et al., "Structure Determination of Cyclopropane–Substituted Acids by Mass Spectrometry," *Journal of Organic Chemistry*, vol. 42, No. 1, pp. 126–129, (Jan. 7, 1977).

Jie, M. S. et al., "Preparation and properties of gem–dichlorocyclopropane derivatives of long–chain fatty esters," *Chemical Abstracts*, vol. 116, No. 17 (1992)—Abstract p. 827 only.

Bianchini, J. P. et al., "Determination of Cyclopropenoic and Cyclopropanoic Fatty Acids in Cottonseed and Kapok Seeks Oils by Gas–Liquid Chromatography," *Analytical Chemistry*, 53(14):2194–2201 (Dec. 1981).

Blanchet, et al., "Chromatographie En Phase Gazeuse et Lipochime", *Oléagineux*, 21° année, No. 12:749–752 (Déc. 1966).

(List continued on next page.)

Primary Examiner—Ellen M. McAvoy
(74) Attorney, Agent, or Firm—Merchant & Gould, PC

(57) ABSTRACT

A process for modifying an unsaturated polyol fatty acid ester stock, such as an unsaturated triacylglycerol oil, to enhance its fluidity and/or oxidative stability is provided. The method includes reacting the unsaturated polyol fatty acid ester stock with cyclopropanating agent. Lubricants containing cyclopropanated polyol fatty acid ester and methods for their production and use are also provided.

52 Claims, 14 Drawing Sheets

OTHER PUBLICATIONS

Christie, W. W., "Cyclopropane and Cyclopropene Fatty Acids," *Topics in Lipid Chemistry*, vol. I, pp. 1–49 (1970).

Christie, W. W. et al., "Mass Spectrometry of Lipids. I. Cyclopropane Fatty Acid Esters," *Lipids*, 1(3):176–182 (May 1966).

Christie, W. W. et al., "Fatty Acids, Part 17. The Synthesis and Chromatographic and Spectroscopic Properties of the Cyclopropane Esters Derived From All the Methyl Octadecenoates", *Chem. Phys. Lipids 2*: 196–202 (1968).

Doering et al., "The Electron–seeking Demands of Dichlorocarbene in its Addition to Olefins", *Jour. of the Amer. Chem. Soc..*, 80:5274–5277 (1958).

Gaydou, E. M. et al., "Fatty Acid Composition of *Sterculia* Seeds and Oils from Madagascar," *J. Agric. Food Chem.* 41(1):64–66 (1993).

Kenney, H. E. et al., "Preparation and Etherification Reaction of Fatty Dichlorocyclopropanes", *The Journal of American Oil Chemists Society*, 41:82–85 (Jan. 1964).

Landgrebe, J. et al., "A Stabilized Cyclopropyl Cation. Synthesis and Solvolysis of 1–Chlorobicyclopropyl", *Journal of the American Chemical Society*, 90:2 395–400 (Jan. 17, 1968).

LeGoff, Eugene, "Cyclopropanes from an Easily Prepared, Highly Active Zinc–Copper Couple, Dibromomethane, and Olefins", *Notes*, 29:2048–2049 (1964).

le Noble, William J., "The Effect of Pressure on the Hydrolysis of Chloroform, Chlorodifluoromethane, and 3–Chloro–3–methylbutyne. The Nature of the Intermediates", *Jour. of the Amer. Chem. Soc.*, vol. 87 (1965).

March, Jerry, "Reactions, Mechanisms, and Structure", *Advanced Organic Chemistry*, $3^{rd}$ Ed., 173–176:768–773 (1985).

Nachtman, E. S. et al., "Lubricants and Lubrication inMetalworking Operations,", Copyright ©Marcel Dekker, Inc., cover pages and pp. 95, 96, 100 and 101 (1985).

Qin, Y. et al., "Effects of the Essential Oil from Litchi Seed on the Serum Lipids Metabolism of Hypercholestrol Rats," *Food Science*, 16(9):56–59 (1995).

Oil Stability Index (OSI), AOCS Official Method Cd 12b–92, pp. 1–5 (Revised 1983).

osi, The Oxidative Stability Instrument, Owners Manual, 3 pgs. (Oct. 1992, revised Mar. 1993).

Overbenger, C. G. et al., "Monomers and Polymers, a Synthesis of Vinyl Cyclopropane and Dicyclopropyl[1]", *Notes*, 28:867–868 (Mar. 1963).

Ralaimanarivo, A. et al., "Fatty Acid Composition of Seed Oils from Six *Adansonia* Species with Particular Reference to Cyclopropane and Cyclopropene Acids," *Lipids*, 17(1), contents page and pp. 1–10 (Jan. 1982).

Rao, K. S. et al., "Fatty Acid and Amino Acid Compositions of *Brachychiton discolor, Brachychiton diversifolius*, and *Brachychiton acerifolius* Seeds," *J. Agric. Food. Chem.*, 37(4):916–920 (1989).

Rao, K. S., "Characteristics and Fatty Acid Composition of *Brachychiton* Species Seeds and the Oils (*Sterculiaceae*)," *J. Agric. Food Chem.*, 39(5):881–882 (1991).

Shortridge, R. W. et al., "The Synthesis of Some Cyclopropane and Spirane Hydrocarbons[1]", *Synthesis of Some Cyclopropane and Spirane Hydrocarbons*, 70:946–949 (Mar. 1948).

Simmons, Howard E. et al., "Cyclopropanes from Unsaturated Compounds, Methylene Iodide, and Zinc–Copper Couple", *Organic Reactions*, 20:1–131 (1973).

Skell, Philip S. et al., "Reactions of Bivalent Carbon Compounds. Reactivities in Olefin–Dibromocarbene Reactions" *Jour. of the Amer. Chem. Soc.*, 78:5430–5433 (Oct. 20, 1956).

Vickery, J.R., "The Occurrence of Dihydromalvalic Acid in Some Seed Oils," *JAOCS*, 58(6):731–732 (Jun. 1981).

Wood, Randall et al., "Cyclopropane Fatty acid Metabolism: Physical and Chemical Identification of Propane Ring Metabolic Products in the Adipose Tissue", *Jour. of the Amer. Oil Chem. Soc.*, 42:315–320 (Apr. 1965).

Woodworth, Curtis W. et al., "Hydrogenolysis of Cyclopropane Derivatives. Application to the Synthesis of an Axial t–Butylcyclohexane, 2–t–Butyladamantane", *Chemical Communications*, pp. 569–570 (1968).

* cited by examiner

Trioleoyl Glycerol Before (A) and After (B) OSI Measurement

Cyclopropanated Trioleoyl Glycerol Before (A)
and After (B) OSI Measurement

CV-75 with 1% TBHQ
Before (A) and After (B) OSI Measurement

Cyclopropanated CV-75 with 1% TBHQ
Before (A) and After (B) OSI Measurement

FIG. 10 DSC Trace of DCCP-FAME

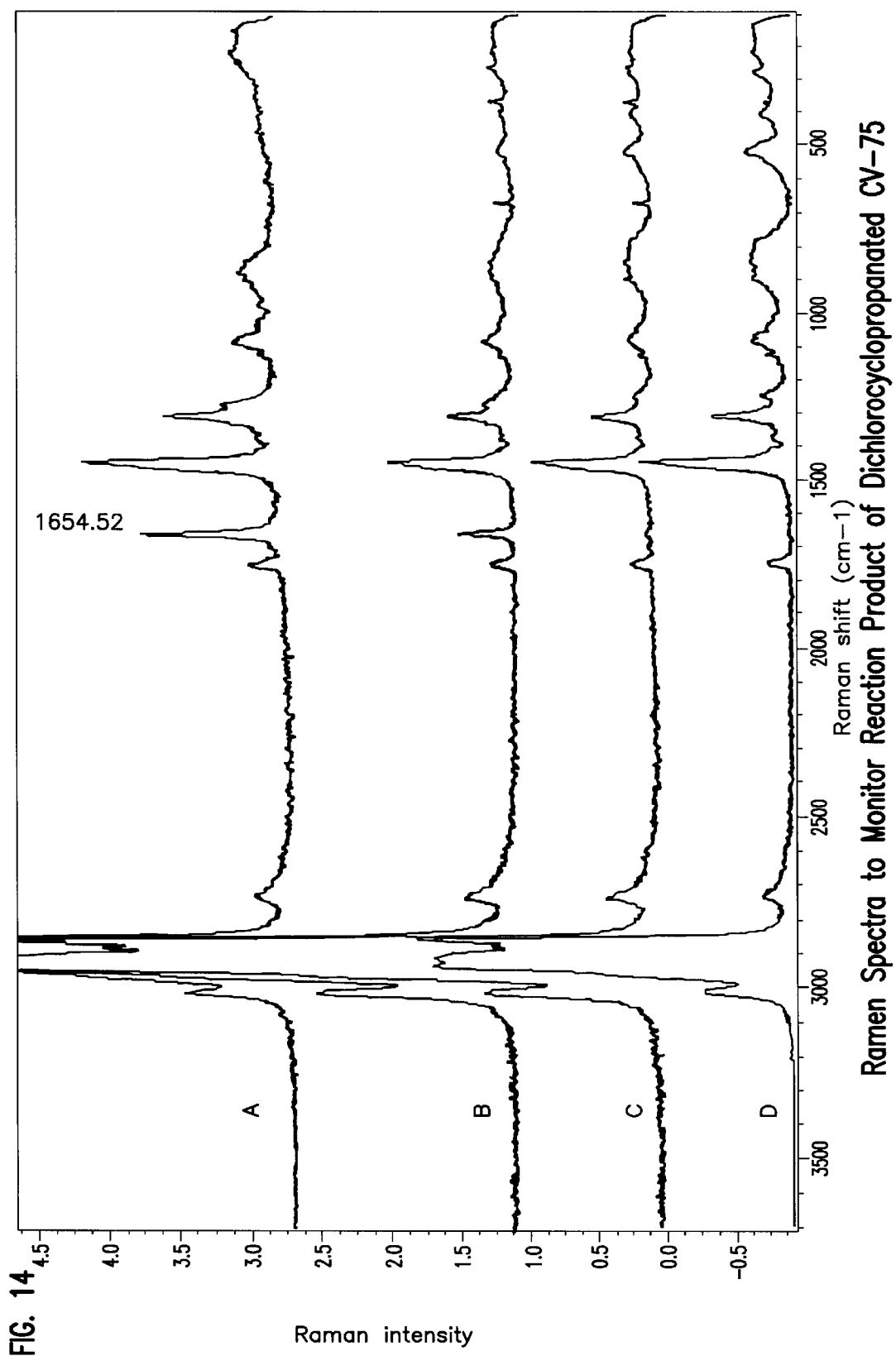

US 6,291,409 B1

PROCESS FOR MODIFYING UNSATURATED TRIACYLGLYCEROL OILS; RESULTING PRODUCTS AND USES THEREOF

This application is a Continuation-In-Part of U.S. patent application Ser. Nos. 09/108,773 (filed Jul. 2, 1998 now U.S. Pat. No. 6,051,539); 60/126,437 (filed Jan. 22, 1999); and 60/118,636 (filed Feb. 4, 1999). The disclosure of each is hereby incorporated by reference herein.

BACKGROUND OF THE INVENTION

Vegetable oils are obtainable in large volumes from renewable resources and in general are characterized as readily biodegradable or "environmentally friendly". As a result, such oils and related unsaturated polyol fatty acid ester stocks are potentially attractive for use in a wide variety of applications.

With respect to use for lubrication purposes, especially as machine lubricants, vegetable oils have not been fully desirable. Many vegetable oils do not possess the desired spectrum of characteristics relating to: pour point; oxidative stability; and compatibility with additives among others. Vegetable oils do however possess many desirable properties for use as a lubricant. In particular, vegetable oils typically provide good boundary lubrication, good viscosity, high viscosity index and high flash point. In addition, vegetable oils are generally nontoxic and readily biodegradable. For example, under standard test conditions (e.g., OCED 301D test method), a typical vegetable oil can biodegrade up to 80% into carbon dioxide and water in 28 days, as compared to 25% or less for typical petroleum-based lubricating fluids.

Two characteristics, which are often major limitations to the utilization of vegetable oils as lubricants, relate to stability and low temperature behavior. In particular, vegetable oils often contain substantial amounts of unsaturation (i.e., one or more carbon-carbon double bonds distributed along the fatty acyl chains). The sites of unsaturation may be associated with sufficient oxidative reactivity to render the oils insufficiently stable for use as lubricants. If efforts are made to reduce the unsaturation, for example by hydrogenation, generally undesirable changes in pour point and/or viscosity index result.

SUMMARY OF THE INVENTION

The present invention relates to modified unsaturated fatty acid and/or ester-based stocks which may be employed as lubricant additives and/or lubricant base stocks. The modified unsaturated fatty acid and/or ester-based stocks may include modified unsaturated polyol fatty acid ester stocks such as cyclopropanated triacylglycerol oils. It particularly concerns modifications of selected vegetable oils to produce liquid products with advantageous properties for use, for example as lubricant base stocks or in related applications. Unsaturated triacylglycerol fatty acid ester stocks are typically derived from plant sources, such as an oil seed, or animal sources, such as tallow.

A process for modifying an unsaturated polyol fatty acid ester stock, such as an unsaturated vegetable oil stock, to enhance its fluidity and/or oxidative stability is provided. The process includes reacting unsaturated polyol fatty acid ester stock with cyclopropanating agent to form a cyclopropanated product. The cyclopropanated product formed from the reaction with the cyclopropanating agent includes polyol fatty acid ester (e.g., triacylglycerols) which has at least one fatty acyl chain modified to include a cyclopropyl group. Polyol fatty acid esters having at least one fatty acyl chain that includes one or more cyclopropyl groups are referred to herein as "cyclopropanated polyol fatty acid esters." It will be understood that the cyclopropanation of the starting ester stock will not necessarily be uniform, but rather may result in cyclopropanation of some fatty acyl chains and not of others. If desired, the cyclopropanated product may be fractionated using conventional techniques to alter the spectrum of modified and unmodified esters present. For example, the cyclopropanated product may be fractionated to remove at least a portion of the saturated esters, thereby enhancing the fluidity properties of the fractionated cyclopropanated product with respect to the cyclopropanated product.

The term "unsaturated polyol fatty acid ester stock" as used herein refers to fatty acid esters of alcohols which include two or more hydroxy groups ("polyols"), where at least some and, typically, a majority (i.e., more than 50%) of the fatty acyl chains include at least one unsaturated carbon-carbon bond. The mixture of fatty acids isolated from complete hydrolysis of a specific unsaturated polyol fatty acid ester stock is referred to herein as a "fatty acid composition." In other words, by the term "fatty acid composition" reference is made to the identifiable fatty acids derived from the fatty acyl residues in the various polyol esters in a given stock. The present unsaturated polyol fatty acid ester stocks typically include esters of a mixture of fatty acids, e.g., a mixture of saturated and unsaturated fatty acids.

Herein, when reference is made to the terms "unsaturated triacylglycerol oil" or "unsaturated triacylglycerol stock," the intent is to refer to a material comprising triacylglycerols, whether altered or not, derived from various plant and animal sources, such as oil seed sources. The unsaturated triacylglycerol oil may also be produced synthetically, e.g., via a reaction between glycerol with fatty acid and/or fatty acid alkyl esters at least a portion of which include unsaturated fatty acyl chains. The term at least includes within its scope: (a) such materials which have not been altered after isolation; (b) materials which have been refined, bleached and/or deodorized after isolation; (c) materials obtained by a process which includes fractionation of an unsaturated triacylglycerol oil; and, also, (d) oils obtained from plant or animal sources and altered in some manner, for example through partial hydrogenation. It will be understood that the unsaturated triacylglycerol oil may include a mixture of triacylglycerols, and a mixture of triacylglycerol isomers. By the term "triacylglycerol isomers", reference is meant to triacylglycerols which, although including the same esterified acid residues, may vary with respect to the location of the residues in the triacylglycerol. For example, an unsaturated triacylglycerol oil such as a vegetable oil stock can include both symmetrical and unsymmetrical isomers of a triacylglycerol which includes two or three different fatty acyl chains (e.g., includes both stearate and oleate groups). This can include triacylglycerol isomers that contain trans as well cis unsaturation and combinations thereof.

Herein, the result of adding cyclopropanating agent to an unsaturated polyol fatty acid ester stock, such as vegetable oil stock, will be referenced as an "cyclopropanated product." The term "cyclopropanated product" includes within its scope the product of reacting one or more cyclopropanating agents (i.e., reagent(s) capable of adding a methylene group to a carbon-carbon double bond to form a cyclopropyl group) with an unsaturated polyol fatty acid ester stock. As noted above, the individual fatty acid esters which include at least one cyclopropyl group are referred to herein as cyclopropanated fatty acid esters. As used herein, the term "cyclopropyl group" refers to an adduct produced by the reaction of cyclopropanating agent with a carbon-carbon double bond, such as a double bond in a fatty acyl chain of a triacylglycerol, to add a methylene moiety and form a three membered ring. One example of a cyclopropanated product is the adduct produced by a Simmons-Smith reaction between $CH_2Br_2$ or $CH_2I_2$ and double bonds in the fatty acyl chain of a vegetable oil stock. The inventors have developed a modified Simmons-Smith reaction for forming a cyclopropanated fatty acid ester. In this method, zinc copper couple is formed in situ using halotrialkylsilane and 1,2-dihaloethane as activators, wherein halogens include chlorine, bromine and iodine and alkyl includes lower alkyls such as methyl, ethyl, butyl and propyl. Preferably, zinc copper couple is formed in situ by contacting zinc and copper halide with chlorotrimethylsilane and 1,2-dibromoethane. Copeer halide includes copper chloride, bromide and iodide. Preferably copper halide is copper(I) chloride. According to this method, the activated zinc is then combined with a mixture of unsaturated polyol fatty acid and dihalomethane, preferably dibromomethane. Another example of a cyclopropanated product is the product resulting from the reaction which takes place upon contacting a haloform (e.g., chloroform ($CHCl_3$) or bromoform ($CHBr_3$)) and base with double bonds present in the fatty acyl chains of unsaturated polyol fatty acid ester stock. Another method of forming a cyclopropanated fatty acid ester stock involves heating a mixture of unsaturated polyol fatty acid ester stock with a trihaloacetate salt, e.g., sodium trichloroacetate or potassium chlorodifluoroacetate. Of course, it will be understood that the cyclopropanation of the unsaturated polyol fatty acid ester stock will not necessarily be uniform in the mixture, but rather the result of the addition may be cyclopropanation of some fatty acyl chains and not to others. Nor will the cyclopropanated product necessarily include the formation of at least one (on an average molecular basis) cyclopropyl group per ester molecule. For example, the cyclopropanated product of a vegetable oil stock may often include a number of triacylglycerols which are not cyclopropanated, i.e., triacylglycerols with fatty acyl chains lacking a cyclopropyl group.

The cyclopropanated polyol fatty acid ester stocks have an oxidative stability (as evidenced by their "Oxidized Viscosity Index" ("OVI"; as defined herein) and/or active methylene content) which is enhanced with respect to the oxidative stability of the corresponding unmodified unsaturated polyol fatty acid ester stock. The enthalpy of melting of the cyclopropanated polyol fatty acid ester stock is generally less than the enthalpy of melting of the starting material or a product obtained from hydrogenation of the unsaturated polyol fatty acid ester stock by a corresponding amount (i.e., an amount which reduces the double bond content of the unsaturated polyol fatty acid ester stock by the same amount as measured by Iodine Value). In most instances, the pour point of a cyclopropanated polyol fatty acid ester stock is reduced with respect to the pour point of the corresponding unsaturated polyol fatty acid ester stock. For example, the present method can reduce the active methylene content of an unsaturated triacylglycerol oil by at least about 10% and preferably by at least about 25% with respect to that of the corresponding unsaturated triacylglycerol oil and at the same time decreases the enthalpy of melting of the cyclopropanated product with respect to the original polyol ester stock.

The cyclopropanating agent used to form the modified fatty acid esters is capable of adding a methylene moiety ("$:CR^2R^3$") to a carbon-carbon double bond form a cyclopropyl group. Examples of suitable cyclopropanating agent include those which are capable of adding a $:CR^2R^3$ methylene moiety to a carbon-carbon double bond, wherein $R^2$ and $R^3$ are typically independently selected from H, halogen, alkyl (commonly lower n-alkyl), phenyl or substituted phenyl. Example of particularly suitable cyclopropanating agents are reagents which are capable of adding a hydrophobic methylene group, e.g., Simmons-Smith type reagents which are capable of adding an unsubstituted methylene moiety ("$:CH_2$") or alkyl substituted methylene moiety ("$:CHR$" or "$:CRR'$" where R and R' are alkyl groups) to the double bond. The inventors have developed a modified Simmons-Smith reaction for forming a cyclopropanated fatty acid ester. In this method, zinc copper couple is formed in situ using halotrialkylsilane and 1,2-dihaloethane as activators, wherein halogens include chlorine, bromine and iodine and alkyl includes lower alkyls such as methyl, ethyl, butyl and propyl. Preferably, zinc copper couple is formed in situ by contacting zinc and copper halide with chlorotrimethylsilane and 1,2-dibromoethane. Copeer halide includes copper chloride, bromide and iodide. Preferably copper halide is copper(I) chloride. According to this method, the activated zinc is then combined with a mixture of unsaturated polyol fatty acid and dihalomethane, preferably dibromomethane. Another type of particularly suitable cyclopropanating agents which may be employed in the present method are combinations of haloform and base. Such reagents are known to react with a carbon-carbon double bond to produce a cyclopropyl group that includes a ring carbon atom substituted with two of the same halogen atoms. The haloform may be chloroform, bromoform, iodoform or a mixture thereof. The base is typically a relatively strong base such as an alkali metal alkoxide and/or hydroxide or an alkali metal hydride. Another method of cyclopropanating an unsaturated polyol fatty acid ester stock includes heating a mixture of the unsaturated ester stock and a trihaloacetate salt. This also can produce cyclopropanated products which are the result of the addition of a dihalocarbene (e.g., ("$:CX_2$" where X is fluoro, chloro, bromo, or iodo)) to a carbon-carbon double bond.

Lubricants which include cyclopropanated fatty acid esters are also provided herein. The lubricants may be produced by processes which include modifying unsaturated polyol fatty acid ester stock modified to have at least one fatty acyl chain including one or more cyclopropyl groups. The process of producing the lubricant may also include blending cyclopropanated polyol fatty acid ester stock with one or more petroleum based lubricating fluids and/or other additives. The dichlorocyclopropanated fatty acid ester can be combined as an additive to a lubricant to form a modified lubricant having improved extreme pressure (E.P.) properties. Preferably, the dichlorocyclopropanated fatty acid ester is included in an amount of about 0.1 wt % to about 20 wt %, more preferably about 5 wt % to about 10 wt %, most preferably about 1 wt % to about 5 wt %.

BRIEF DESCRIPTION OF THE DRAWINGS

FIG. 14 shows Raman spectra of (A) untreated CV-75; (B) DCCP reaction end product using chloroform (8.3 molar equivalents per double bond), solid NaOH (1.1 molar equivalents per double bond), and benzyltriethylammonium chloride (0.01 molar equivalents per double bond), room temperature, 1 hr.; (C) DCCP reaction end product using chloroform (8.3 molar equivalents per double bond), solid NaOH (3.3 molar equivalents per double bond), and benzyltriethylammonium chloride (0.01 molar equivalents per double bond), room temperature, 15 min.; and (D) DCCP reaction end product using chloroform (7.5 molar equivalents per double bond), 50% NaOH (7.5.0 molar equivalents per double bond), and benzyltriethylammonium chloride (0.01 molar equivalents per double bond), 55° C., 6 h (identical to FIG. 13(F)).

DETAILED DESCRIPTION

Figure 1:
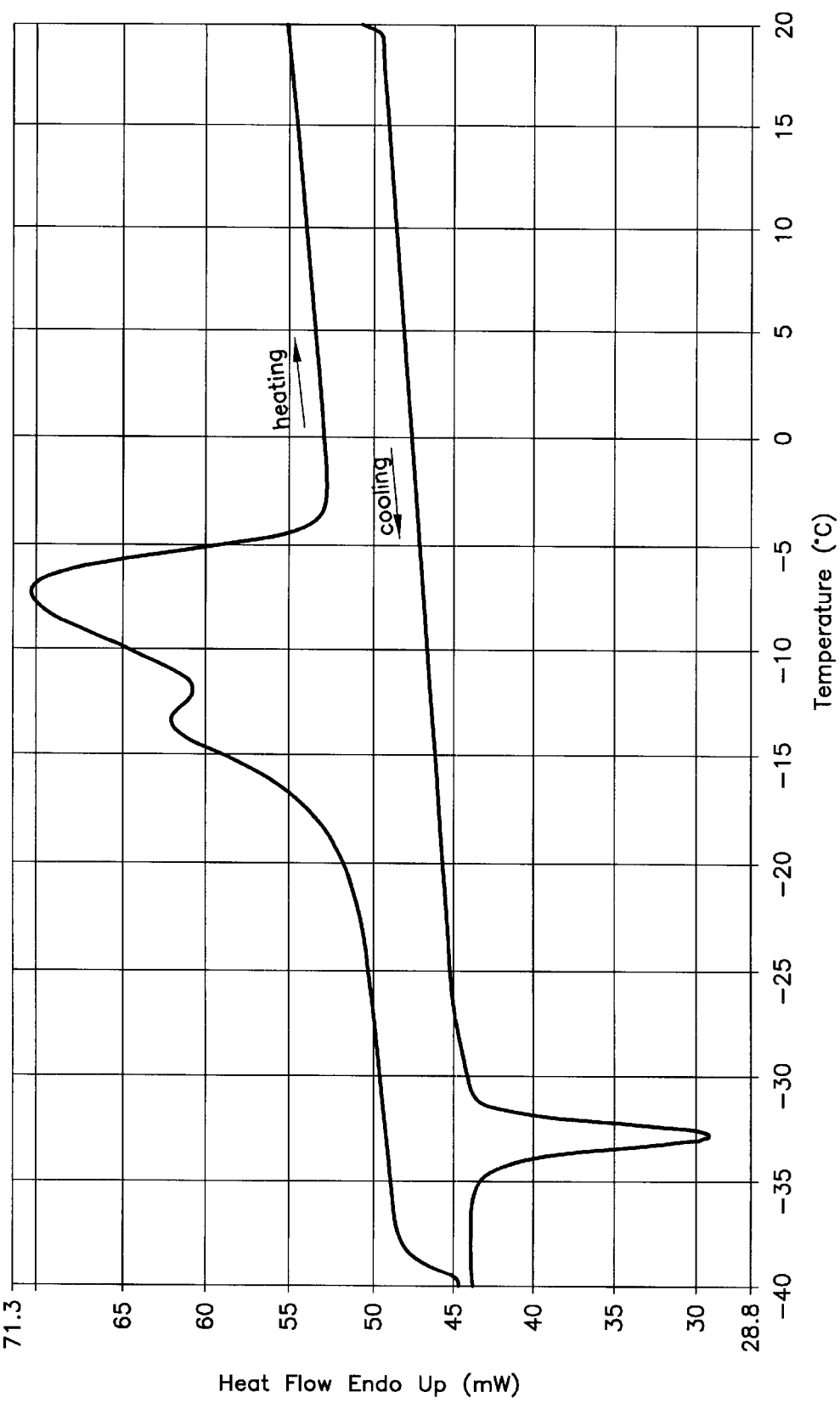
FIG. 1 shows a differential scanning calorimetry ("DSC") trace observed on cooling a sample of trioleoylglycerol from 0° C. to −40° C. at 1.00° C./min (lower curve) and then, after holding the sample at −40° C. for ten minutes, reheating the sample to 20° C. at a rate of 5.00° C./min (upper curve).

The present method may be utilized to increase the fluidity and/or enhance the oxidative stability of unsaturated fatty acid ester stocks, such as unsaturated triacylglycerol oils. For example, the method allows the production of vegetable oil based lubricants which, in addition to possessing very attractive lubricating properties, are environmentally friendly. Since polyol fatty acid ester based lubricant base stocks are typically derived from natural materials, these lubricants can have low toxicity and are generally readily biodegraded.

I. UNSATURATED POLYOL FATTY ACID ESTER STOCKS

Unsaturated polyol fatty acid ester stocks include one or more unsaturated fatty acid esters and may also include one or more saturated fatty acid esters. Typically, the present unsaturated fatty acid ester stocks include a mixture of esters of saturated and unsaturated fatty acids, e.g., a mixture of saturated and unsaturated triacylglycerols such as high oleic canola oils. The polyol ester stocks are made up of fatty acid esters of alcohols which include two or more hydroxy groups ("polyols" or "polyhydric alcohols"). Fatty acid esters which are formed from polyhydric alcohols typically have all of the hydroxy groups esterified. Such esters include at least two fatty acyl chains and preferably one fatty acyl chain per hydroxy group. Esters in which a portion of the hydroxy groups are esterified with a short chain carboxylic acid (i.e., carboxylic acids such as acetic and propionic acid which contain no more than 5 carbon atoms) are also included within the present definition of fatty acid esters. Typically no more than about 5 wt. % of the corresponding fatty acid composition and preferably much less is made up of short chain carboxylic acid(s). Preferably, all but one and, more preferably, all of the hydroxy groups of the alcohol portion of the esters are esterified to a fatty acyl group. As employed herein, the term "fatty acyl group" refers to acyl groups ("—C(O)R") which include an aliphatic chain (linear or branched) typically having from about 6 to about 30 carbon atoms.

Polyols which can be used to form the present unsaturated fatty acid esters include at least two and, preferably, at least three hydroxy groups per molecule. Typically, the polyols have no more than about 6 hydroxy groups per alcohol molecule and include up to about 20 carbon atoms and preferably no more than about 8 carbon atoms. Examples of suitable aliphatic polyols include glycerol, alkylene glycols (e.g., ethylene glycol, diethylene glycol, triethylene glycol and neopentylglycol), pentaerythritol, trimethylolethane, trimethylolpropane, and sorbitol. Suitable alicyclic polyols include cyclohexanediols and inositol as well as natural cyclic polyols such as glucose, galactose and sorbose.

Fatty acid esters of polyols which include no more than about 6 carbon atoms and have three to six hydroxy groups per molecule, such as glycerol, pentaerythritol, trimethylolethane, trimethylolpropane, sorbitol, inositol, glucose, galactose, and/or sorbose, are particularly suitable for use in the present invention. Preferably, such esters have a fatty acid composition which includes at least about 90 wt. % fatty acyl groups with aliphatic chains having from about 16 to 20 carbon atoms. The unsaturated fatty acid ester stocks typically employed in the present process have an Iodine Value of no more than about 150 and preferably no more than about 130. The amount of cyclopropyl groups in a polyol ester stock can be characterized based on the average number of cyclopropyl groups per fatty acyl chain (referred to herein as the "average cyclopropyl content"). The unsaturated fatty acid ester stocks may be modified to have an average cyclopropyl content of at least about 0.25 (i.e., an average of at least about 0.25 cyclopropyl groups per fatty acyl chain) and, preferably, at least about 0.4.

Unlike petroleum-based lubricants, polyol fatty acid esters, such as triacylglycerols, have slight polarity on one end of the molecule due to the presence of the ester linkages. In some instances, this can be desirable when the material is used as a lubricating fluid, since the polar end of triacylglycerol molecules can become attracted to a metallic surface, while the nonpolar hydrocarbon region will generally project outwardly from metallic surfaces. This causes, in some instances, molecular attraction and alignment, and can result in better boundary lubrication ("thin film") with increased load carrying capacity and reduction in wear.

While the unsaturated fatty acid ester stocks employed in the present invention typically include fatty acid esters of polyhydric alcohols, for some applications, the unsaturated stock may be primarily made up of fatty acid esters of monohydric alcohols ("monoesters"). For example, fatty acid monoester stocks may be used as a fuel with enhanced lubrication properties in comparison to conventional petroleum fuels. For such applications, the esters typically include an acyl chain having from 10 to 24 and, preferably from 16 to 22 carbon atoms. The alcohol portion of the ester molecules generally includes no more than about four carbon atoms and preferably is a methyl or ethyl ester. In one embodiment of the invention, unsaturated fatty acid monoester stock (e.g., an unsaturated monoester stock produced by esterifying a fatty acid mixture derived from hydrolysis of an oil seed stock with a C(1–6) alcohol) may be modified by reaction with a cyclopropanating agent which includes haloform (e.g., chloroform) and base. Such a fatty acid monoester stock can also be cyclopropanated by decomposing a trihaloacetate salt (e.g., thermally) with the stock.

II. PROPERTIES OF UNSATURATED TRIACYLGLYCEROL OILS

Unsaturated triacylglycerol oils include triacylglycerol molecules (sometimes termed triglycerides). In general, triacylglycerols comprise three long fatty acid chains esterified to glycerol; or, alternatively phrased, glycerol esterified by addition thereto of three long chain fatty acids. Herein, the terms "triacylglycerols" and "triglycerides" are intended to be interchangeable, and will in some instances be referred to by the abbreviation "TAG".

As indicated above, any given triacylglycerol molecule generally includes glycerol esterified with three fatty acid molecules. Thus, each triacylglycerol includes three fatty acid residues. In general, oils extracted from any given plant or animal source comprise a mixture of triacylglycerols, characteristic of the specific source. The mixture of fatty acids isolated from complete hydrolysis of the triacylglycerols in a specific source are generally referred to as a "fatty acid composition". By the term "fatty acid composition" reference is made to the identifiable fatty acid residues in the various triacylglycerols. The distribution of specific identifiable fatty acids is typically characterized by the amounts of the individual fatty acids as a weight percent of the total mixture of fatty acids obtained from hydrolysis of the particular oil stock.

For example, the fatty acid composition of CV-75, a typical high oleic canola oil is as shown in Table I below.

TABLE I

Fatty Acid Composition of
Typical High Oleic Canola Oil

| Fatty acid | Weight Percent[1] |
| --- | --- |
| Palmitic acid | 4.0 |
| Stearic acid | 3.0 |
| Oleic acid | 74.0 |
| Linoleic acid | 11.5 |
| Linolenic acid | 4.5 |
| Other | 3.0 |

[1]Weight percent of total fatty acid mixture derived from hydrolysis of CV-75.

Palmitic and stearic acids are saturated fatty acids and triacylglycerol acyl chains formed by the esterification of either of these acids do not contain any carbon-carbon double bonds. However, many fatty acids such as oleic acid, linoleic acid and linolenic acid are unsaturated. Oleic acid is an 18 carbon fatty acid with a single double bond; linoleic acid is an 18 carbon fatty acid with two double bonds or points of unsaturation; and linolenic acid is an 18 carbon fatty acid with three double bonds. More specifically, oleic acid is (Z)-9-octadecenoic acid;

linoleic acid is (Z,Z)-9,12-octadecadienoic acid;

alpha-linolenic acid is (Z,Z,Z)-9,12,15-octadecatrienoic acid; and gamma-linolenic acid is the (Z,Z,Z)-6,9,12 isomer of octadecatrienoic acid.

The average number of double bonds present per fatty acyl chain in an unsaturated polyol fatty acid ester is referred to herein as the "average unsaturation content." For example, the average unsaturation content of an unsaturated triacylglycerol oil may be calculated based from the distribution of fatty acids in the mixture produced by hydrolysis of the triacylglycerols. The distribution of fatty acids in a particular oil may be readily determined by methods known to those skilled in the art. Unsaturated triacylglycerol oils which are particularly suitable for use as starting materials in the present methods generally have an average unsaturation content of no more than about 1.7 and, preferably, about 0.4 to about 1.3 per fatty acyl chain.

As an example, on average, each triacylglycerol molecule in CV-75 contains about 3.3 double bonds, distributed among the various fatty acyl chains (three chains in each triacylglycerol molecule), i.e., CV-75 has an average unsaturation content of about 1.1 per acyl chain. This results from the fact that CV-75 includes a mixture of triacylglycerols and the triacylglycerol molecules of CV-75 generally each have a mixture of fatty acid residues.

Another measure for characterizing the average number of double bonds present in a polyol fatty acid ester stock (such as the triacylglycerol molecules of an unsaturated triacylglycerol oil) is its Iodine Value. The Iodine Value of a triacylglycerol or mixture of triacylglycerols is determined by the Wijs method (A.O.C.S. Cd 1-25). The present method can be used to improve the fluidity and oxidative stability of unsaturated triacylglycerol oils having a wide range of Iodine Values. Typically, however, the present methods employ as starting materials unsaturated polyol fatty acid ester stocks, such as vegetable oil stocks, having an Iodine Value of no more than about 150, preferably about 70 to about 140, and, more preferably, about 80 to about 110.

For example, high oleic canola oil typically has an Iodine Value of about 85 to about 110 and a pour point of about −10° C. to −15° C. Hydrogenation of such oils to reduce its Iodine Value to about 75 or less can improve the oxidative stability of the oil. Hydrogenated oils with this level of Iodine Value, however, generally have substantially decreased fluidity as evidenced by an increase in pour point to about 10 to 30° C. or higher and can become solids at room temperature thereby limiting their use as a functional fluid.

During use and/or storage lubricants tend to break down due to oxidation or other degradation processes. When employed as a functional fluid, such as a lubricating fluid, a vegetable oil may oxidize during which polymerization and degradation occurs. Polymerization increases viscosity and reduces lubrication functionality. Degradation leads to breakdown products that may be volatile or corrosive. In either case, undesirable modifications to the lubricating characteristics of the fluid occur.

One measure of the oxidative stability of a polyol fatty acid ester stock is the effect on viscosity observed after passing an oxygen-containing gas through a heated sample of the oil stock. For example, the viscosity of a sample may be measured after passing a controlled flow of air through a sample of oil heated to 110° C. according to the procedure described in A.O.C.S. Method Cd 12b-92. The relative stability of the sample can be characterized in a number of ways, e.g., the amount of time required to achieve a specified increase in viscosity or by measuring the change in viscosity after passing air through the heated sample for a designated period of time. The term "Oxidized Viscosity Index" ("OVI") as used herein refers to the amount of time required to produce an 500 cP increase in viscosity in a sample which has been treated under the conditions described in A.O.C.S. Method Cd 12b-92. For example, the present fatty acid ester stocks generally have an OVI of at least about 50 hours, and more preferably of at least about 100 hours.

The term "$OV_X$" is used herein to refer to the viscosity of a sample treated under the oxygenation conditions described in A.O.C.S. Method Cd 12b-92 for a preset length of time ("X" in hours). Thus, "$OV_{50}$" refers to the viscosity of a sample after passing air through a 110° C. sample at about 140–150 mL/min for 50 hours. Preferably, the cyclopropanated products of the present invention have an $OV_{50}$ of no more than about 500 cP and, more preferably, no more than about 300 cP.

The conditions of lubricating fluid storage and/or use, which may involve exposure to substantial heat; pressure; metal surfaces, etc., can facilitate the oxidation process. It is desirable, then, to use lubricating fluids which are not readily susceptible to undesirable levels of oxidation and/or polymerization, at least under normal storage and use conditions. Unsaturated fatty acyl chains are more readily susceptible to oxidation than saturated fatty acyl chains. Thus, triacylglycerols such as those found in vegetable oils, which contain substantial amounts of oleic acid, linoleic acid and/or linolenic acid residues, can be subject to undesirable levels of oxidation and/or polymerization.

The undesirable levels of oxidative instability are presently believed to be due in large part to the presence of unsaturated fatty acyl chains and, in particular, polyunsaturated fatty acyl chains that contain "active methylene groups." As used herein, active methylene groups refers to —$CH_2$— groups which are situated between two double bonds in a fatty acyl chain, i.e., doubly allylic —$CH_2$— groups. When found, the active methylene groups are typically present in dienic and trienic polyunsaturated fatty acyl chairs. Active methylene groups are principally present in polyunsaturated fatty acid-containing triacylglycerol molecules, e.g., linoleic esters (with one active methylene group) and linolenic esters (with two active methylene groups). The term "active methylene content" as used herein refers to the average number of active methylene groups per fatty acyl chain in a polyol fatty acid ester such as an unsaturated triacylglycerol oil. The active methylene content of an unsaturated triacylglycerol oil can be calculated based from the fatty acid composition of the unsaturated triacylglycerol oil. For example, it can be calculated based on the fatty acid composition listed in Table I that CV-75 contains an average of about 0.2 active methylene groups per fatty acyl chain.

It has been found that the oxidative stability, particularly as it relates to lubricating applications, of an unsaturated polyol fatty acid ester stock is substantially enhanced if the cyclopropanated stock has an active methylene content of no more than about 0.5, preferably no more than about 0.3 and, more preferably, no more than about 0.1. For example, cyclopropanation of vegetable oil to reduce its active methylene content to no more than about 0.3 typically enhances the oxidative stability of the cyclopropanated adduct with respect to the original stock.

Of course, the propensity for a triacylglycerol to oxidize can also be reduced by hydrogenation of the double bond(s). That is, as the extent of hydrogenation increases (and the Iodine Value and active methylene content decrease), the propensity toward oxidation decreases. Unfortunately, however, hydrogenation generally is accompanied by concomitant, and undesirable, increase in "pour point", i.e., reduction in the fluidity of the oil. For example, a saturated triacylglycerol, tristearin (the stearic acid triester of glycerol; stearic acid is octadecanoic acid; $C_{18}H_{36}O_2$), has a melting point of 74° C., compared to melting points of 5° C. for triolein and −11° C. for trilinolein.

It is apparent, then, that one cannot simply hydrogenate an unsaturated triacylglycerol oil such as vegetable oil to obtain an oxidatively stable lubricating fluid. Thus, although vegetable oils exhibit many properties desirable in a lubricating fluid, such oils have generally not been acceptable due to propensity toward oxidation and the resulting increase in viscosity, and if hydrogenated, undesirable levels of loss of fluidity (or increase of pour point).

In general, similar affects are observed with a variety of vegetable oils. For example, palm oil, which has a low average unsaturation content (e.g., an Iodine Value of about 40 to 60), is a semi-solid at room temperature and is generally not useful as a lubricant despite its relatively good oxidative stability. On the other hand, linseed oil has a very high level of polyunsaturation (fatty acyl groups containing more than one double bond), an Iodine Value of 170 to 180 and a low pour point. Due to the propensity of linseed oil to crosslink or polymerize, unsaturated triacylglycerol oils used to produce a lubricant base stock by the present methods typically do not include a significant amount of linseed oil, e.g., less than about 25 wt. %, preferably no more than about 10 wt. %, and most preferably are substantially free (i.e., less than about 0.1 wt. %) of linseed oil.

Because of the tendency of unsaturated fatty acid esters stocks having very high levels of polyunsaturation to polymerize, plant or animal derived oil stocks having an active methylene content of no more than about 1.0 and/or an Iodine Value of no more than about 150 are typically used to produce lubricant base stocks using the present method. Preferably, the starting unsaturated fatty acid ester stock has an active methylene content of no more than about 0.8, preferably no more than about 0.65 and/or includes no more than about 15 wt. % (on a fatty acid composition basis), preferably no more than about 10 wt. % of trienic (i.e., having three double bonds) unsaturated fatty acid ester groups, such as esters of linolenic acid.

III. MODIFICATIONS TO UNSATURATED POLYOL FATTY ACID ESTER STOCKS FOR USE AS LUBRICATING FLUIDS

A. General

The fluidity of a material is in part determined by the ability of molecular packing, intermolecular interactions, and molecular weight. In general, increasing branching of a hydrocarbon, especially towards the methyl end, or introducing unsaturation in the chain increases fluidity since it disrupts packing. By "increase in fluidity" in this context, reference is meant to reduction in "pour point" or "melting point". The term "pour point" as used herein refers to the temperature at which the material stops flowing (as measured by ASTM method D 97). Thus pour point is a property which may involve a phase change but generally is based on a change in the viscosity properties of the material. The term "melting point" as used herein refers to the temperature at which a material transforms from a solid to a liquid, i.e., when a phase change involving a heat of fusion occurs.

In addition to pour point, the viscosity of an unsaturated polyol fatty acid ester stock (such as an unsaturated triacylglycerol oil or modified version thereof) at room temperature or an elevated temperature (e.g., 40° C.) may be used to characterize its fluidity. Unless otherwise indicated, viscosities reported herein are in centipoise (cP) as determined using a Brookfield viscometer type R.V.F. at a 20 rpm setting. The present cyclopropanated products typically have a viscosity at 40° C. of no more than about 200 cP and, preferably, no more than about 100 cP.

Introducing cis unsaturation into a fatty acyl chain typically produces a greater increase in fluidity than the introduction of a trans double bond since it disrupts packing to a greater extent. One advantage of the present method, is that the majority of cyclopropanation reagents add a methylene moiety to a carbon-carbon double bond in a manner that preserves the stereochemistry of the double bond, i.e., a cis disubstituted double bond is generally converted into a cis disubstituted cyclopropyl group. This is extremely advantageous since the majority of double bonds in naturally occurring fatty acyl chains have a cis configuration. Thus, the present method removes a double bond from a fatty acyl chain, thereby decreasing the propensity of the fatty acyl group towards oxidation and/or polymerization, while preserving the advantageous effect of a cis configuration ("kinking effect") on fluidity properties. The enthalpy of melting of a sample is indicative of the amount of energy necessary to transform the sample from a solid to a liquid. A decrease in enthalpy of melting provides a good indication that the sample has been modified to have less ordered packing. The present cyclopropanated products typically have an enthalpy of melting which is at least about 10 J/g and, preferably, at least about 50 J/g lower than that of the unsaturated polyol fatty acid ester stock.

For some lubricants, the desired fluidity properties may be specified in terms of a viscosity index (as determined by ASTM method D 2270). For example, it is characteristic of triacylglycerol oils that their viscosity fluctuations as a function of temperature change to a lesser extent than the viscosities of petroleum based mineral oils. The viscosity-to-temperature properties of each oil can be characterized in terms of the viscosity index ("VI"). A higher viscosity index signifies that the viscosity of the oil concerned changes less as a function of changes in temperature. The viscosity indexes of triacylglycerols (typically in the range of about 180 to about 225) are clearly higher than those of petroleum based mineral oils with no additives (typically 50–120), so that triacylglycerols are to their nature so-called multigrade oils. This is of considerable importance under conditions in which the operating temperature may vary within rather wide limits. Modified unsaturated triacylglycerol oils produced by the present methods generally have a viscosity index which is quite similar to the original triacylglycerol oil. Preferably, the present modified unsaturated triacylglycerol oils have a viscosity index of at least about 130 and, more preferably, at least about 140. This is typically achieved by selecting a starting unsaturated triacylglycerol oil which has close to the viscosity index desired for the modified product.

As part of the development of the present techniques, it was theorized that triacylglycerols having therein substantial sites of unsaturation could be improved, with respect to fluidity, by generation of cyclopropyl groups, i.e., moieties extending from at least some of the long acyl chains. It was foreseen that such cyclopropyl groups would limit the ability for the fatty acyl chains to pack closely. At the same time, a cyclopropyl group generated via a cyclopropanation reaction would remove a double bond from the acyl chain backbone. This can create at least two benefits: (i) a decrease in the possibility of double bond migration to generate a less stable polyunsaturated chain, e.g., through the formation of a conjugated diene or triene fatty acyl chain; and (ii) decrease the possibility of volatile degradation products being generated through oxidative cleavage. In addition, as mentioned above, the cyclopropanation reaction generally preserves a cis configuration present in the original double bond and the associated "kinking effect." Thus, it was theorized that through cyclopropanation, a desirable lubricating fluid could result which would possess appropriate characteristics with respect to both stability towards oxidation and, desirably, low pour point or melting point.

B. Cyclopropanated Adducts

Modification of unsaturated triacylglycerol oils through formation of a cyclopropanated product can increase the oxidative stability with respect to the unmodified vegetable oil stock, e.g., increase the "Oxidized Viscosity Index" ("OVI") by at least about 50%. Preferably, the formation of a cyclopropanated product can be used to increase the OVI of an unsaturated polyol fatty acid ester by a factor of at least about 2 (i.e., increased by at least about 100%) with respect to the corresponding unmodified unsaturated polyol fatty acid ester.

It has been found that cyclopropanation may be used to modify unsaturated polyol fatty acid ester, such as triacylglycerol oils, to improve their properties as lubricating fluids. It can be theorized that when a cyclopropanating agent is reacted with polyol fatty acid ester having an unsaturation therein, a methylene moiety is added to a carbon-carbon double bond or point of unsaturation in the unsaturated ester stock to form a cyclopropyl group.

The modified esters of the present invention may be produced by reacting a cyclopropanating agent with at least a portion of the carbon-carbon double bonds of an unsaturated fatty acid ester stock. The cyclopropanating agent is capable of of reacting with the double bond to add a methylene moiety (":$CR^2R^3$") and produce a cyclopropyl group. Depending on the nature of the cyclopropanating agent, the methylene moiety which is added may be unsubstituted (i.e., ":$CH_2$") or may be substituted with one or two substituents. While a wide variety of cyclopropanating agents are known to those skilled in the art, the cyclopropanating agent is preferably capable of reacting with the double bond to produce a hydrophobic cyclopropyl group.

In addition to an unsubstituted methylene moiety, examples of of suitable cyclopropyl groups include those substituted with halogen, alkyl and/or phenyl (optionally substituted with one or more common substituents such as halogen, lower alkoxy, lower alkyl, cyano, carboxyalkyl and/or haloalkyl). Preferably, the cyclopropanating agent is capable of adding a :$CR^2R^3$ methylene moiety to form the cyclopropyl group where $R^2$ and $R^3$ are independently selected from H, F, Cl or Br. Most preferably, the cyclopropanating agent is capable of adding :$CH_2$, :$CF_2$, :$CCl_2$ and/or :$CBr_2$ to a carbon-carbon double bond to form a cyclopropyl group.

One suitable class of cyclopropanating agent are those which are capable of adding a :$CH_2$ methylene moiety to the double bond via a Simmons-Smith type reaction. Such cyclopropanating agents typically include zinc reagent and a gem-dihaloalkane, e.g., R'CHXY where X is bromo or iodo, Y is chloro, bromo or iodo, and R' is hydrogen or alkyl, more preferably, n-C(1–6)alkyl. Particularly suitable dihalomethanes for use in the Simmons-Smith type reaction include $CH_2Br_2$ and $CH_2I_2$. The zinc reagent typically includes zinc dust, zinc-copper couple ("Zn(Cu)"), zinc-silver couple ("Zn(Ag)"), or dialkyl zinc (e.g., diethyl zinc). The alkyl groups of the dialkyl zinc reagent are typically lower alkyl groups (i.e., alkyl groups having one to six carbon atoms) and preferably are n-C(1–6) alkyl groups. The zinc reagent may optionally include a lewis acid (e.g., titanium(IV) chloride) which is capable of enhancing the reactivity of the zinc reagent.

Suitable techniques for generating cyclopropanating agents include: (A) reacting diiodomethane with zinc-copper couple ("Zn(Cu)") in an ether solvent ("method A"); (B) reaction of a diazoalkane with zinc halides in an ether solvent ("method B"); and (C) reaction of diiodomethane or a gem-diiodoalkane with diethylzinc in ether or hydrocarbon solvents ("method C").

Cyclopropanation of unsaturated fatty acid esters using diiodomethane (Method A) has the advantage of being simple, convenient and economical. Furthermore, this method is relatively mild (slightly exothermic) and therefore is preferable for use in a large scale reaction. Cyclopropanation of unsaturated fatty acid esters using dibromomethane and zinc copper couple activated by chlorotrimethylsilane and 1,2-dibromoethane (a modification to Method A) is also a slightly exothermic proceedure that is suitable for use in a large scale reaction. Furthermore, this method is relatively inexpensive and does not require separate preparation of a zinc-copper couple.

Scheme 1

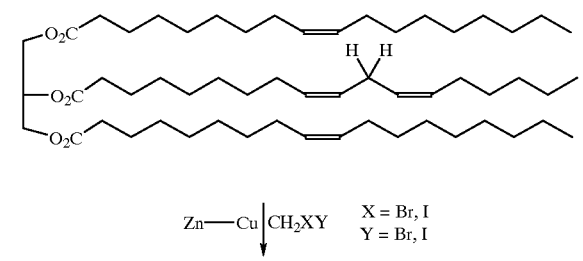

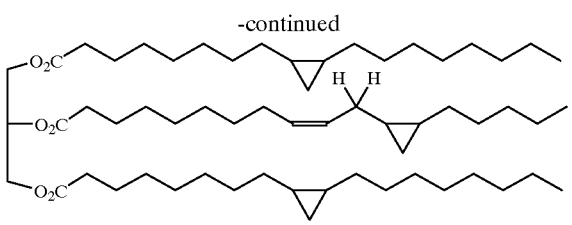

As illustrated in Scheme 1, a cyclopropanating agent can react with a double bond in one of the fatty acyl chains of a triacylglycerol. The reaction may occur at a double bond in either a fatty acyl chain esterified at a primary hydroxyl group of the glycerol (e.g., the :$CH_2$ adduct shown in Scheme 1) or in a fatty acyl chain esterified at a secondary hydroxyl group of the glycerol (e.g., the :$CH_2$ adduct shown in Scheme 1). The formation of a cyclopropyl groups lowers the Iodine Value or average unsaturation content of the unsaturated triacylglycerol oil by removing a point of unsaturation, i.e., the number of double bonds present per triacylglycerol molecule is decreased by the cyclopropanation reaction. In addition, the number of active methylene groups present can be reduced by cyclopropanation of a polyunsaturated acyl chain of a polyol fatty acid ester. For example, the reaction of a Simmons-Smith reagent with the C12-double bond of a linoleic ester chain as shown in Scheme 1, destroys the allylic character of the methylene group at the 11 position. Moreover, as discussed herein, contrary to what is observed with hydrogenation, cyclopropanation leads to a product having a lower enthalpy of melting.

As illustrated in Scheme 1, there are a variety of cyclopropanated adducts that can be formed from the addition of a single "methylene moiety" to an unsaturated triacylglycerol oil. It is expected that reaction between the cyclopropanating agent and an unsaturated triacyglycerol could occur at one or more of a number of positions along a fatty acyl chain. The reaction may also occur with double bonds on one or more of the fatty acyl chains within a triacylglycerol molecule. By way of illustration, a cyclopropanation reaction of vegetable oil to produce a cyclopropanated product can be carried out by a variety of methods such as those described in Simmons et al., "Organic Reactions," vol. 20, pp. 1–131 (1973) and March, "Advanced Organic Chemistry," 3rd edition, John Wiley & Sons, New York, N.Y., pp. 170–176, 768–771 (1985).

One particularly suitable method of cyclopropanating an unsaturated fatty acid ester stock is to react the stock with haloform and a base. The reaction which occurs upon contacting an unsaturated polyol fatty acid ester with haloform and base results in the addition of a dihalomethylene moiety to a carbon-carbon double bond to produce a cyclopropyl group that includes a ring carbon atom substituted with two of the same halogen atoms. The haloform may be chloroform ($CHCl_3$), bromoform ($CHBr_3$), or iodoform ($CHI_3$) or a mixture thereof. The base is typically a relatively strong base such as an alkali metal alkoxide (e.g., potassium t-butoxide) and/or hydroxide (e.g., sodium and/or potassium hydroxide), alkaline earth hydroxide (e.g., calcium hydroxide), or an alkali metal hydride (e.g., sodium hydride). A particularly suitable method of employing cyclopropanating agents of this type is to form a mixture of haloform and the unsaturated ester. The mixture is then contacted with a relatively concentrated (e.g., at least about 25 wt. %) aqueous solution of alkali metal hydroxide and/or alkaline earth hydroxide in the presence of a phase transfer catalyst. Suitable examples of phase transfer catalysts include tetraalkyl ammonium salts and tetraalkyl phosphonium salts where the alkyl groups altogether have a total of at least about 10 carbon atoms and inclusion complexes (e.g., crown ethers). Common phase transfer catalyst may include one or more aralkyl groups (e.g., benzyl or phenethyl) substituted for one or more of the alkyl groups. One example of suitable phase transfer catalyst is a benzyltrialkylammonium halide, such as benzyltriethylammonium chloride. Typically the haloform includes chloroform and the base is an aqueous sodium hydroxide solution (preferably at least about 25 wt. % sodium hydroxide). The cyclopropanating agent is allowed to react with the unsaturated ester at a temperature of about 20° C. to about 100° C., and preferably of about 40° C. to about 75° C. The reaction is carried out for a sufficient period of time to form the desired amount of cyclopropanated adduct while attempting to minimize the amount of degradation of the polyol ester due to reaction of the base with the ester groups. This can be accomplished, for example, by reacting unsaturated polyol ester dissolved in haloform with 50 wt. % sodium hydroxide at 50° C. to 60° C. for 4–6 hours in the presence of phase transfer catalyst. Scheme 2 shows an illustrative reaction of a triacylglycerol ("OLO") with chloroform and sodium hydroxide to form a polyol ester that includes four dichlorocyclopropyl groups.

In an alternate embodiment, solid sodium hydroxide can be used in place of aqueous sodium hydroxide. This can be accomplished by reacting unsaturated polyolester dissolved in haloform with solid alkali metal hydroxide at room temperature for about 30 minutes in the presence of a phase transfer catalyst. Solid alkali metal hydroxide is preferably solid sodium hydroxide. The solid alkali metal hydroxide can be used in either (or both) powder and crystal forms. Advantages of this method include easy work-up of the reaction product and a considerable reduction in reaction time.

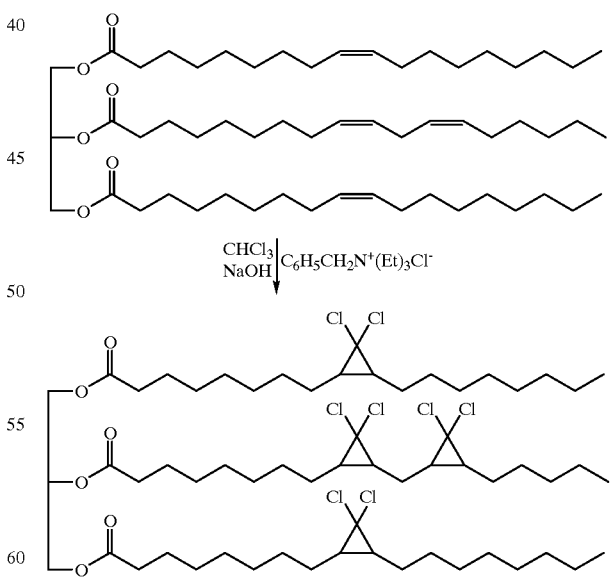

Scheme 2

Another method suitable for cyclopropanating an unsaturated fatty acid ester stock is to heat a mixture of the stock and a salt of a trihaloacetic acid. For example, heating an alkali metal salt of trichloroacetic acid or chlorodifluoroacetic acid in the presence of a compound which contains a carbon-carbon double bond results in a product corresponding to the addition of a dihalocarbenoid to at least a portion of the double bonds present. One example of such a reaction is shown in Scheme 3. Heating a mixture of unsaturated triacylglycerol and sodium chlorodifluoroacetate in a suitable solvent such as diglyme provides a product resulting from the addition of a difluorocarbenoid type species (":CF$_2$") to one or more of the carbon-carbon double bonds present in the fatty acyl chains of the triacylglycerol. Similarly, heating a mixture of triacylglycerol and sodium trichloroacetate would results in the conversion of carbon-carbon double bonds into dichlorocyclopropyl groups.

The cyclopropanation reaction, it is believed, has at least two beneficial affects. First, it helps to reduce the susceptability of the unsaturated triacylglycerol oil to oxidation. In addition, the presence of the resulting cyclopropyl groups in the fatty acyl chains appears to decrease the ease of packing and thus helps to maintain a low pour point or melting point.

It is important to recognize that in commercial practice of the techniques described herein, the techniques will typically be operated on mixtures of triacylglycerols either isolated as a plant or animal oil, e.g., by various oil seeds processing techniques, or resulting from alteration of such oils, for example by prior partial hydrogenation.

Scheme 3

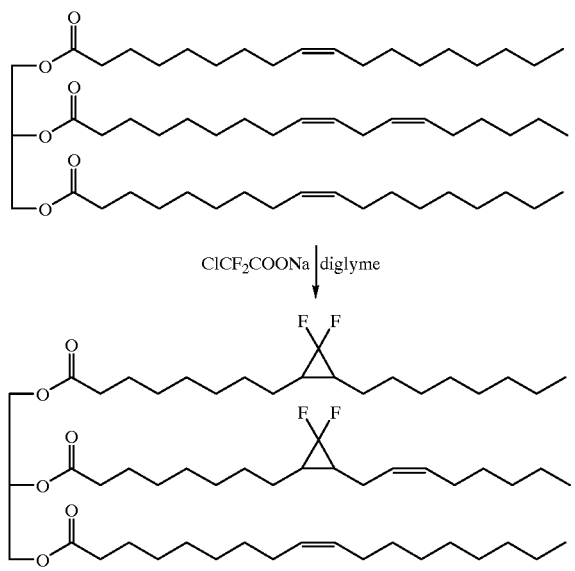

Herein, when it is said that the "unsaturated polyol fatty acid ester stock" or "unsaturated triacylglycerol oil" contains an average of at least one double bond per triacylglycerol (or triacylglycerol) molecule therein ("unsaturation content"), reference is meant to the average double bond presence in the triacylglycerol mixture, on a per fatty acid chain basis. An unmodified high oleic canola oil, as indicated above, generally contains an average of about 3.3 double bonds per molecule and about 1.1 double bonds per acyl chain. Examples of other unmodified vegetable oils and fish oils include those listed in Table II below (together with typical Iodine Values for the oils). Additional examples include high monounsaturated containing oils (e.g., high oleic oils such as CV-75). Of course, the "unsaturated triacylglycerol oil" is employed in applications according to the present invention may include a mixture of oils from a variety of sources.

TABLE II

| Unsaturated Triacylglycerol Oil | Iodine Value |
|---|---|
| Rapeseed oil | 97–108 |
| Corn oil | 103–128 |
| Peanut oil | 84–100 |
| Safflower oil | 140–150 |
| Olive oil | 80–88 |
| Soybean oil | 120–130 |
| Sunflower oil | 125–136 |
| Cottonseed oil | 99–113 |
| Menhaden oil | 150–160 |
| Herring oil | 115–160 |

Herein, in connection with cyclopropanation of the unsaturated fatty acid ester stock, reference will in some instances be made to "at least partially cyclopropanating". By this, it is meant that the starting unsaturated polyol ester stock is treated under appropriate conditions to add a methylene group to at least some of the double bonds to form cyclopropyl groups. In order to be considered "at least partially cyclopropanated" as the term is used herein, there should be a reduction of at least about 10%, and preferably at least about 25% of the total number of double bonds (on an average per fatty acyl chain basis for the whole cyclopropanated product). The term "on an average per fatty acyl chain basis" in this connection, is meant to refer to on an average per fatty acyl chain over all the triacylglycerol molecules in the reaction mixture, whether those fatty acyl chains include a cyclopropyl group or are unreacted fatty acyl chains.

From the above, it will be understood that the intent is to reference techniques that may be practiced on mixtures, without precise analysis of exact adduct and unreacted triacylglycerol presence in the mixture, but rather with a general understanding of overall cyclopropanation during modification. The intent, in general, is to obtain a stock of desirable property with respect to, inter alia, pour point and stability. Indeed, it is foreseen that in some applications blends may well be desirable, depending on the use to which the lubricating stock is to be placed. The present method is particularly useful for producing lubricant base stocks which include a predominant amount of a modified unsaturated triacylglycerol oil, e.g., a lubricant base stock including at least about 50 wt. % and, preferably, at least about 75 wt. % of the modified unsaturated triacylglycerol oil. By employing the present method, biodegradable, triacylglycerol oil-based stocks which have a combination of oxidative stability and viscosity properties suitable for a variety of lubricant applications may be produced. Preferred embodiments of the invention include such oil stocks having an oxidative stability characterized by an OVI of at least about 50 hours, preferably at least about 100 hours, and/or an active methylene content of no more than about 1.5, preferably no more than about 1.0 and, more preferably, no more than about 0.5. Preferred base stocks typically are fluid at room temperature and have a viscosity index of at least about 125 and/or a viscosity at 40° C. of no more than about 200 cP and, preferably, no more than about 125 cP.

The present cyclopropanated esters can be produced by a variety of permutations of the present method. A number of such permutations are shown in Scheme 4. In addition, to direct cyclopropanation of an unsaturated polyol fatty acid ester stock as described herein, the fatty acid esters may be modified through hydrolysis, reesterification and/or transesterification. As illustrated in Scheme 4, such modifications may take place either prior to or after the cyclopropanation step. For example, an unsaturated triacylglycerol stock may be transesterified with another alcohol, e./g., a polyol such as trimethylolpropane or neopentyl glycol, prior to cyclopropanation. Alternatively, the triacylglycerol stock may be first hydrolyzed to the corresponding mixture of fatty acids ("fatty acid composition"). The cyclopropanation reaction may be carried out directly on the resulting fatty acids. The cyclopropanated fatty acids may be employed as components in lubricants. For example, salts of dichlorocyclopropanated fatty acids may be employed as anionic emulsifiers in aqueous based metal working fluids. In yet another variation of the method, the cyclopropanated fatty acids can be esterfied with a desired alcohol (polyol and/or monohydric alcohol) to provide a cyclopropanated fatty acid ester stock. In still another variation, the fatty acids may be converted into alkyl esters ("monoesters") which may be cyclopropanated and used as is or transesterified into cyclopropanated polyol esters.

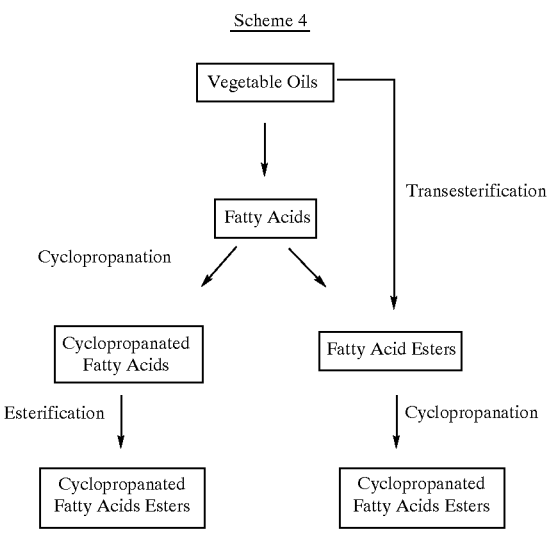

Scheme 4

1. Some Preferred Vegetable Oils

Techniques according to the present invention, as will be understood from the experimental report below, were particularly developed for generation of desirable lubricating fluids from vegetable oils. In general, this is because of the particular level of unsaturation found in many vegetable oils, as well as the physical properties both of starting materials and the final adducts. In general, improvement is observed if the extent of cyclopropanation is such that at least about 0.2 cyclopropyl groups are added per fatty acyl chain, on average. Generally, reactions to the extent of 0.3 to 0.75 cyclopropyl groups added, per fatty acyl chain, will be preferred (i.e., an average cyclopropyl content of 0.3 to 0.75). This can readily be controlled by judicious choice of the starting vegetable oil stock, the type and amount of cyclopropanation agent employed and the reaction conditions. More broadly, improvement in the oxidative stability of an unsaturated polyol ester stock, such as a vegetable oil stock, can be produced through the addition of at least about 0.1 cyclopropyl groups on average per fatty acyl chain. It has been found that the cycloaddition up to about 2.0 cyclopropyl groups on average per triacylglycerol molecule can generally produce a substantial enhancement in the oxidative stability of the unsaturated triacylglycerol oil.

Particularly suitable vegetable oils for use with the present method include high oleic oils, i.e., oils which have a fatty acid composition containing at least about 50 wt. % oleic acid. Other vegetable oils which, it is foreseen, may be modified with techniques according to the present invention, include: rapeseed oil, olive oil, sunflower oil, soybean oil, safflower oil, peanut oil, cottonseed oil, crambe oil, mustard oil, and meadowfarm oil. As used herein, "rapeseed oil" includes high erucic acid rapeseed oil ("HEAR") and low erucic acid rapeseed oil ("LEAR" or canola oil). Variants of some of the other oils listed above are also known, e.g., high oleic and very high oleic sunflower, canola and soybean oils. As discussed herein, these vegetable oils may be employed in the present invention as isolated or in altered form, as well as with oil from a single source or mixtures of one or more of the types of oils (or altered forms thereof).

IV. SOME PREFERRED PRODUCTS

A. Lubricating Fluid Base

Techniques according to the present invention can be utilized to prepare preferred lubricating fluid bases, or base stocks, from various plant or animal oils. As indicated above, a vegetable oil derivative can be prepared, for example, as a lubricating base stock. Lubricating base stocks would, in general, be fluids that can be used as the ingredient present in the highest amount by weight in a wide variety of lubricating fluids, for example, as the base fluid stock for crankcase oils, transmission oils, power transfer fluids (e.g., hydraulic fluids), gear oils and greases. It is foreseen that such materials may be used as the lubricating fluid base in such industries as: the automotive industry, metal working and metal forming industries, earth moving industry, and general manufacturing.

B. Preparation of Lubricating Fluids from the Base Stock

The major constituent of a lubrication fluid is a base oil (base stock) formulated with small amounts of additives. The base oil provides the primary lubricant functionality and performance. The additives enhance the performance of the base oil and also provide additional advantages and/or remove the shortcomings of the base oil.

Once base stocks according to the present invention are developed, they can be readily converted into lubricating fluid by the provision therein of appropriate additives. For example, to make lubricants, such as motor oils, transmission fluids, gear oils, industrial lubrication oils, metal working oils, and the like, one typically starts with a lubricant grade of the present modified unsaturated polyol fatty acid ester stock (also referred to collectively herein as a "cyclopropanated base stock"). Into this "base stock" is typically blended a small amount of specialty chemicals that can enhance lubricity, inhibit wear and corrosion of metals, and retard damage to the fluid from heat and oxidation.

As previously indicated, the modified polyol esters of the present invention are useful in preparing lubricants, particularly lubricants based on synthetic lubricating oils and mixtures thereof. The compositions of the invention can be employed in a variety of lubricants based on diverse oils of lubricating viscosity, including natural and other synthetic lubricating oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. The lubricants can also be used in natural gas engines, stationary power engines and turbines and the like. Automatic or manual transmission fluids, transaxle lubricants, gear lubricants, both for open and enclosed systems, tractor lubricants, metal working lubricants, hydraulic fluids and other lubricating oil and grease compositions also can be prepared with compositions of the present invention. The polyol esters may also be used in lubricants for wirerope, walking cam, slideway, rock drill, chain and conveyor belt, worm gear, bearing, and rail and flange applications.

The lubricating oil compositions of the present invention include modified unsaturated polyol ester as described herein and, in addition, typically include at least one other oil of lubricating viscosity which is different from the ester (A). Typical lubricating oil compositions of the invention include about 10 to about 95 wt. % of the polyol ester (A) and about 5 to about 90 wt. % of an oil of lubricating viscosity other than the ester (A). Such lubricating oil compositions also may, and preferably, contain antioxidant and other performance additives as described herein. The amount of the antioxidant and other performance additives included in the lubricating oil composition typically ranges from about 0.01% to about 10% more often from about 0.1% to about 7% or 8%. The amount of the antioxidant in other performance additives included in the lubricating oil compositions will depend on the use for which the lubricant is designed, and such amounts can be readily determined by those skilled in the art.

The lubricating compositions and methods of this invention employ an oil of lubricating viscosity other than the polyol esters (A) described above, and such oils include natural or synthetic lubricating oils and mixtures thereof. Natural oils include animal oils, vegetable oils (including high oleic vegetable oils), products derived from vegetable oils (e.g., rapeseed oil reacted with methanol in the presence of a catalyst forms rapeseed fatty acid methyl ester), mineral lubricating oils, solvent or acid treated mineral oils, hydro-refined mineral oil and hydrocracked mineral oils. Synthetic lubricating oils include hydrocarbon oils (poly-alpha-olefins), halo-substituted hydrocarbon oils, alkylene oxide polymers, esters of mono- and dicarboxylic acids and polyols, esters of phosphorus-containing acids, polymeric tetrahydrofurans and silicon-based oils. Unrefined, refined, and rerefined oils, either natural or synthetic, may be used in the compositions of the present invention. A description of oils of lubricating viscosity occurs in U.S. Pat. No. 4,582,618 (column 2, line 37 through column 3, line 63, inclusive), herein incorporated by reference for its disclosure to oils of lubricating viscosity.

One embodiment of the present invention which may be useful in particular as a metal working lubricant is an emulsifiable lubricant fluid that includes cyclopropanated fatty acid salt stock. The cyclopropanated fatty acid salt typically includes fatty acid salt having a fatty acyl chain which includes at least one halogenated cyclopropyl group and, preferably, one or more dichlorinated cyclopropyl group(s). Typically, the fatty acid salt stock has an average cyclopropyl content of at least about 0.25 and is primarily composed of fatty acid salts (and/or derivatives) having fatty acyl chains with 10 to 24 carbon atoms and, preferably, chains having 16 to 22 carbon atoms. The fatty acid salts commonly are salts of one or more alkali metal atoms.

In one embodiment of the invention, the lubricating compositions can have an SAE gear viscosity number of at least about SAE 65, more preferably at least about SAE 75. The lubricating composition may also have a so-called multigrade rating such as SAE 75W-80, 75W-90, or 80W-90. Multigrade lubricants may include a viscosity improver which is formulated with the oil of lubricating viscosity to provide the above lubricant grades.

In another embodiment, the oil of lubricating viscosity is selected to provide lubricating compositions for crankcase applications, such as for gasoline and diesel engines. Typically, the lubricating compositions are selected to provide an SAE crankcase viscosity number of 10W, 20W, or 30W lubricants. The lubricating composition may also have a so-called multi-grade rating such as SAE 5W-30, 10W-30, 10W-40, 20W-50, etc. As described above, multi grade lubricants can include a viscosity improver which is formulated with the oil of lubricating viscosity to provide the above lubricant grades.

Other Lubricant Components

The compositions of this invention, and particularly, the lubricating oils, functional fluids, and greases of the invention may contain performance additives, such as antioxidants, detergents, dispersants, metal deactivators, antiwear agents, extreme-pressure agents, viscosity index modifiers, pour point depressants, foam inhibitors, demulsifiers, friction-modifiers, and/or corrosion-inhibitors. Some of the antioxidants described above also function as antiwear agents, extreme-pressure agents, or corrosion-inhibitors, but supplemental antiwear agents, extreme-pressure agents and corrosion-inhibitors often are desirable in the compositions of the invention.

A wide variety of antioxidant compositions can be used in combination with the polyol esters of the invention. Examples of various types of antioxidants which can be used in combination with the polyol esters include sulfur-containing compositions, aromatic amines including alkylated aromatic amines, phenols, oil-soluble transition metal containing compounds, etc. More particularly, the antioxidants useful in the present invention may be selected from phenolics, aromatic amines, phenothiazines, dithiophosphates, dithiocarbamates, sulfides, sulfurized olefins, sulfurized oils including vegetable oils, sulfurized fatty acids or esters, sulfurized Diels-Alder adducts, and tocopherols.

Small amounts of antioxidants can interact with the polyol ester stocks of the present invention to provide stabilized polyol ester stocks. Generally, the polyol esters can be stabilized with up to 5% by weight, based on the weight of the polyester of one or more antioxidants and more often, amounts of 3% or less of antioxidant is effective in significantly improving the stability of the polyol esters.

Metal deactivators which may be included in the present lubricant compositions generally include triazole-containing compound(s) and more particularly, benzotriazole and/or substituted benzotriazole(s). A wide variety of aromatic triazoles are known, many of which are described in detail in "Benzotriazole: A Novel Synthetic Auxiliary," Katritsky, Rachwal and Hitchings, Tetrahedron, Vol. 27, No. 16/17, p. 2683–2732, 1991 (Pergamon Press pic), along with methods for their preparation.

Suitable detergents for use in the present compositions are exemplified by oil-soluble neutral and basic salts (i.e. over-based salts) of alkali, alkaline earth, or transition metals with sulfonic acids, carboxylic acids, including hydrocarbyl substituted carboxylic acylating agents, phenols or organic phosphorus acids. The hydrocarbyl-substituted carboxylic acylating agents include agents which have a hydrocarbyl group derived from a polyalkene, such as polybutene. The polyalkenes can include homopolymers and interpolymers derived from one or more olefins. The polyalkene is generally characterized as containing from about 8 up to about 300 carbon atoms. In one embodiment, the polyalkene is typically characterized by an Mn (number average molecular weight) of about 500 to about 5000.

Suitable antiwear, extreme-pressure, friction modifiers and corrosion-inhibiting agents include chlorinated aliphatic hydrocarbons, such as chlorinated wax; alkyl-substituted succinic acids or anhydrides reacted with alkylene oxides such as ethylene oxide or propylene oxide; sulfurized alkylphenols; phosphosulfurized hydrocarbons, such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentyl phenyl phosphite, dipentyl phenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; boron-containing compounds including borate esters; dimercaptothiadiazole derivatives; amino-mercaptothiadiazole derivatives; and molybdenum compounds. Many of the above-mentioned antioxidants can also serve as extreme-pressure agents and corrosion-inhibitors.

Pour point depressants are an additive which is also often included in the lubricating oils described herein. Examples of useful pour point depressants are polymethacrylates; polyacrylates; polyacrylamides; condensation products of haloparaffin waxes and aromatic compounds; minerol oils; fatty acid alkyl esters; petroleum based hydrocarbons; vinyl carboxylate polymers; styrene-maleic anhydride copolymer esters; and polymers of dialkylfumarates, vinyl esters of fatty acids and alkyl vinyl ethers.

Antifoam agents are used to reduce or prevent the formation of stable foam. Typical antifoam agents include silicones or organic polymers. Additional antifoam compositions are described in "Foam Control Agents," by Henry T. Kerner (Noyes Data Corporation, 1976), pages 125–162.

Suitable viscosity improvers include but are not limited to polyolefins, such as ethylene-propylene copolymers, polyisobutenes, or polybutylene; rubbers, including hydrogenated rubbers, such as styrene-butadiene or styrene-isoprene rubbers; polyacrylates, including polymethacrylate acid esters and polyacrylate acid esters; diene polymers, polyalkyl styrenes, alkenyl aryl conjugated diene copolymers (preferably styrene-maleic anhydride copolymer esters), hydrogenated isoprenoids and multifunctional viscosity improvers. Particularly suitable viscosity improvers include polyolefin or polymethacrylate. Commercially available viscosity improvers include Acryloid™ viscosity improvers available from Rohm & Haas; Shellvis™ rubbers available from Shell Chemical; hydrogenated polyisoprenoids from Kurary Co.; and Lubrizol 3174 available from the Lubrizol Corporation.

The amount and type of additives required in a formulation depends upon the severity of the application; usually the additives vary from 5 to 20% of the total formulation. Types of additives that commonly used in lubricant formulations include: viscosity index improvers (e.g., a few % polyisobutylenes and/or polymethacrylates); oxidation inhibitors (e.g., 0.5–1.0% di-tert-butyl-p-cresol and/or other phenolic antioxidant); pour point depressants (e.g., circa 1% of a polymethacrylate); antiwear agents (e.g., a few % of a polar fatty acid compound and/or a zincdiorganodithiophosphate); detergent dispersants (e.g., 2–20% of a sulfonate and/or a phosphate); and rust inhibitors (e.g., circa 1% of a mildly polar organic acids, organic phosphates and/or amines).

The invention will be further described by reference to the following examples. These examples illustrate but do not limit the scope of the invention that has been set forth herein.

IV. ILLUSTRATIVE EXPERIMENTAL EXAMPLES

Example 1

Cyclopropanation of Trioleoylglycerol

To a suspension of 100 g of freshly prepared zinc-copper couple (III) in dry diethyl ether (500 mL) stirred mechanically under reflux was added dropwise a solution of 130 g of trioleoylglycerol and 433 g of diiodomethane in dry diethyl ether (100 mL) using a pressure-equalized addition funnel. The resulting mixture was stirred under reflux for 4 h and cooled down to room temperature. The precipitates were filtered off and the ether solution was washed with 1.0 N HCl (300 mL) and water (2×300 mL). The solvent was removed using a rotatory evaporator and the excess amount of diiodomethane was removed at ~70° C. under high vacuum to provide 140 g of the cyclopropanated trioleoylglycerol. The cyclopropanated trioleoylglycerol had an Iodine Value of 4.36 as compared to the Iodine Value of 83.5 for the starting trioleoylglycerol.

This is a slightly exothermic procedure that is mild and suitable for use in large scale reactions.

$^1$H-NMR (cyclopropanated trioleoylglycerol) (300 MHz, CDCl$_3$) 5.26 (m, 1H), 4.31–4.10 (m, 4H), 2.30 (t, 6H, J=7.5 Hz), 1.28–1.25 (m, 78H), 0.86 (t, 9H, J=6.6 Hz), 0.63–0.51 (m, 10H), −0.33 to −0.37 (m, 2H)

$^{13}$C-NMR (cyclopropanated trioleoylglycerol) (75.4 MHz, CDCl$_3$) 173.2, 172.8, 68.8, 62.1, 34.2, 34.0, 31.9, 30.2, 30.1, 29.7, 29.5, 29.4, 29.3, 29.1, 29.0, 28.7, 28.6, 24.9, 24.8, 22.7, 15.8, 15.7, 14.1, 10.9.

Raman Shift (cm$^{-1}$) (cyclopropanated trioleoylglycerol, neat): 3066, 2994, 2932, 2896, 2855, 1747, 1442, 1396, 1298.

IR (cm$^{-1}$) (cyclopropanated trioleoylglycerol, neat): 3080, 3000, 2932, 1032.

$^1$H-NMR (trioleoylglycerol) (300 MHz, CDCl3) 5.34–5.30 (m, 7H), 4.31–4.10 (m, 4H), 2.30 (t, 6H, J=7.5 Hz), 2.00–1.96 (m, 12H), 1.28–1.25 (m, 66H), 0.86 (t, 9H, J=6.6 Hz).

$^{13}$C-NMR (trioleoylglycerol) (75.4 MHz, CDCl$_3$) 173.2, 172.8, 129.9, 129.6, 68.8, 62.1, 34.1, 34.0, 31.9, 29.8, 29.7, 29.5, 29.2, 29.1, 29.0, 27.2, 27.1, 24.9, 24.8, 22.7, 14.1.

Raman Shift (cm$^{-1}$) (trioleoylglycerol, neat): 3010, 2927, 2896, 2855, 1747, 1659, 1437, 1303, 1262.

IR (cm$^{-1}$) (trioleoylglycerol, neat): 3010.

Example 2

Cyclopropanation of a High Oleic Canola Oil

To a suspension of 100 g of freshly prepared zinc-copper couple (III) in dry diethyl ether (500 mL) stirred mechanically under reflux was added dropwise a solution of 130 g of CV-75 (a high oleic canola oil stock commercially available from Inter Mountain Canola, Idahofalls, Id.) and 433 g of diiodomethane in dry diethyl ether (100 mL) using a pressure-equalized addition funnel. The resulting mixture was stirred under reflux for 4 h and cooled down to room temperature. The precipitates were filtered off and the ether solution was washed with 1.0 N HCl (300 mL) and water (2×300 mL). The solvent was removed using a rotatory evaporator and the excess amount of diiodomethane was removed at ~70° C. under high vacuum to provide 140 g of cyclopropanated CV-75.

This is a slightly exothermic procedure that is mild and suitable for use in large scale reactions.

Raman Shift (cm$^{-1}$) (cyclopropanated CV-75, neat): 3066, 2994, 2932, 2896, 2855, 1747, 1442, 1396, 1298, 1215.

IR (cm−1) (cyclopropanated CV-75, neat): 3080, 3000, 2932, 1032.

Raman Shift (cm−1) (CV-75, neat): 3010, 2927, 2896, 2855, 1747, 1659, 1437, 1303, 1262.

IR (cm−1) CV-75, neat): 3010.

Example 3

DSC of Cyclopropanated Adducts

Figure 2:
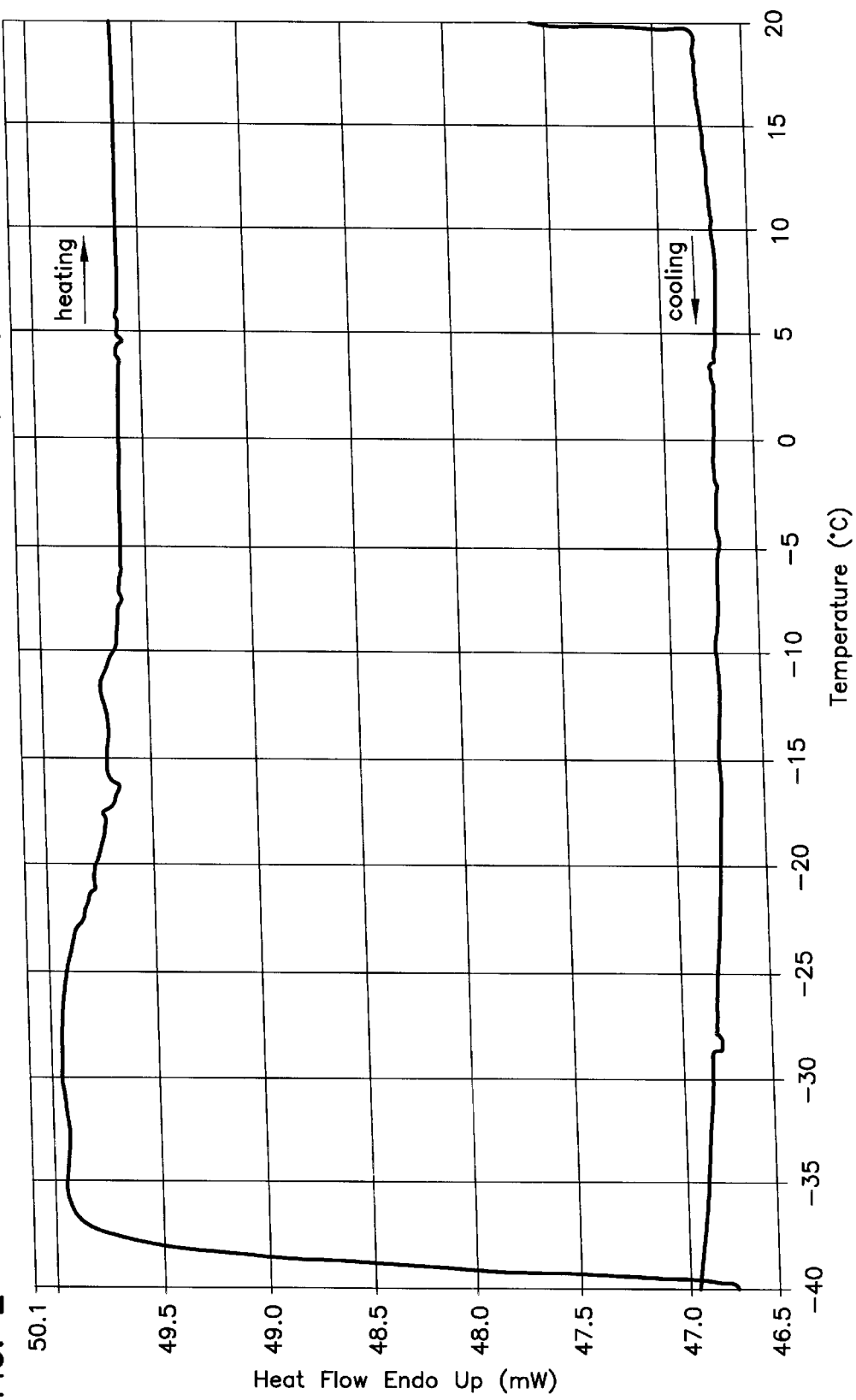
FIG. 2 shows a DSC trace observed on cooling a sample of cyclopropanated trioleoylglycerol from 0° C. to −40° C. at 1.00° C./min (lower curve) and then, after holding the sample at −40° C. for ten minutes, reheating the sample to 20° C. at a rate of 5.00° C./min (upper curve).

Differential scanning calorimetry ("DSC") samples of trioleoylglycerol, cyclopropanated trioleoylglycerol, CV-75, and cyclopropanated CV-75 were prepared and loaded at room temperature. The crystallization temperature ($T_c$), melting temperature ($T_m$) and ΔH were determined for these samples using the following sequence: a) hold the sample at 20° C. for 10.0 min; b) cool the sample to −40° C. at a rate of 1.00° C./min; c) hold the sample at −40° C. for 10.0 min; d) heat the sample to 20° C. at a rate of 5.00° C./min. The DSC results are summarized below. FIGS. 1 and 2 show the DSC curves obtained for trioleoylglycerol and cyclopropanated trioleoylglycerol respectively. The results demonstrate that cyclopropanation can substantially decrease the enthalpy of melting of a vegetable oil.

Cyclopropanated trioleoylglycerol: Tc=not observed; Tm=−20–−22° C.; ΔH=2 J/g.

Trioleoylglycerol: Tc=−33° C.; Tm=−5° C.; ΔH=72 J/g.

Cyclopropanated CV-75: Tc=not observed; Tm=−10° C.; ΔH=4 J/g.

CV-75: Tc=−40° C.; Tm=−7° C.; ΔH=67.5 J/g.

Example 4

Oxidative Stability of Cyclopropanated Adducts

The oxidative stability of the cyclopropanated products produced in Examples 1 and 2 as well as the corresponding starting materials (trioleoylglycerol and CV-75) were determined by treating samples using the procedure described in A.O.C.S. Method Cd 12b-92. The Oxidized Viscosity Index ("OVI") was measured by passing a controlled flow of air through a heated sample of the oil. The degradation of the sample under such conditions typically includes an induction phase followed by a large increase in the rate of oxidation and/or polymerization with an associated large increase in the viscosity of the sample after this point. The viscosity after the induction phase was complete and the length of time (to the nearest hour) required for the oil sample to complete the induction period is reported below. The results shown below demonstrate that cyclopropanation can substantially increase the oxidative stability of a vegetable oil.

Viscosity Before and After Oxidative Stability Testing

Trioleoylglycerol:
  Untreated: 80 cP;
  After OSI: 1494 cP (3.65 hr).
Cyclopropanated trioleoylglycerol:
  Untreated: 190 cP;
  After OSI: 277 cP (16.05 hr).
CV-75 with 1% TBHQ:
  Untreated: 68 cP;
  After OSI: circa 1500 cP (150.4 hr).
Cyclopropanated CV-75 with 1% TBHQ:
  Untreated: 194 cP;
  After OSI: 300 cP (211.75 hr).

The viscosity results were corroborated by examining the Raman spectra of the various samples before and after being subjected to Oxidative Stability Index testing conditions ("OSI"). The results are shown in FIGS. 3–6.

Figure 3:
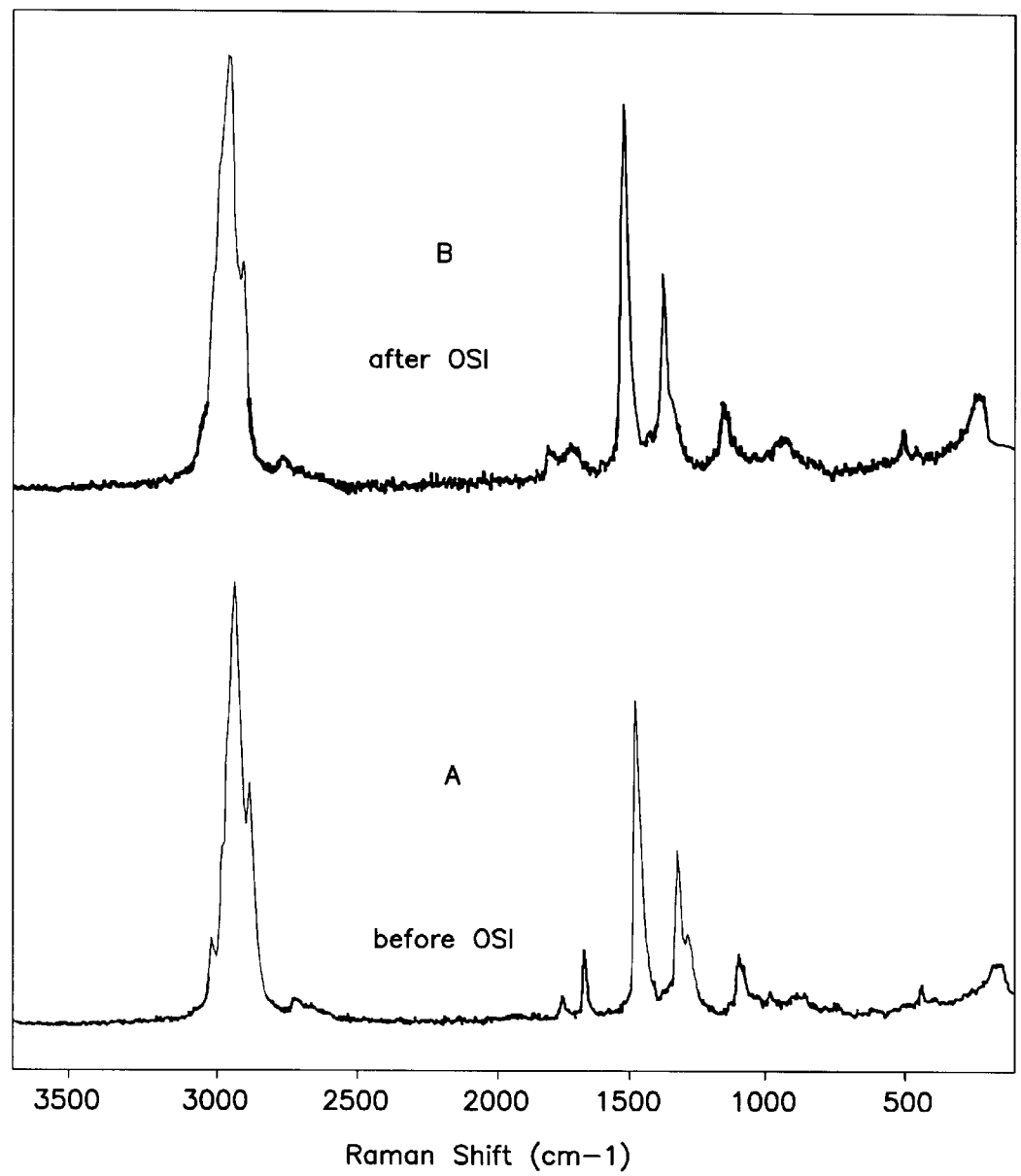
FIG. 3 shows Raman spectra of (A) untreated trioleoylglycerol; and (B) trioleoylglycerol after being treated by passing air through a 110° C. sample for 3.65 hours.
Figure 4:
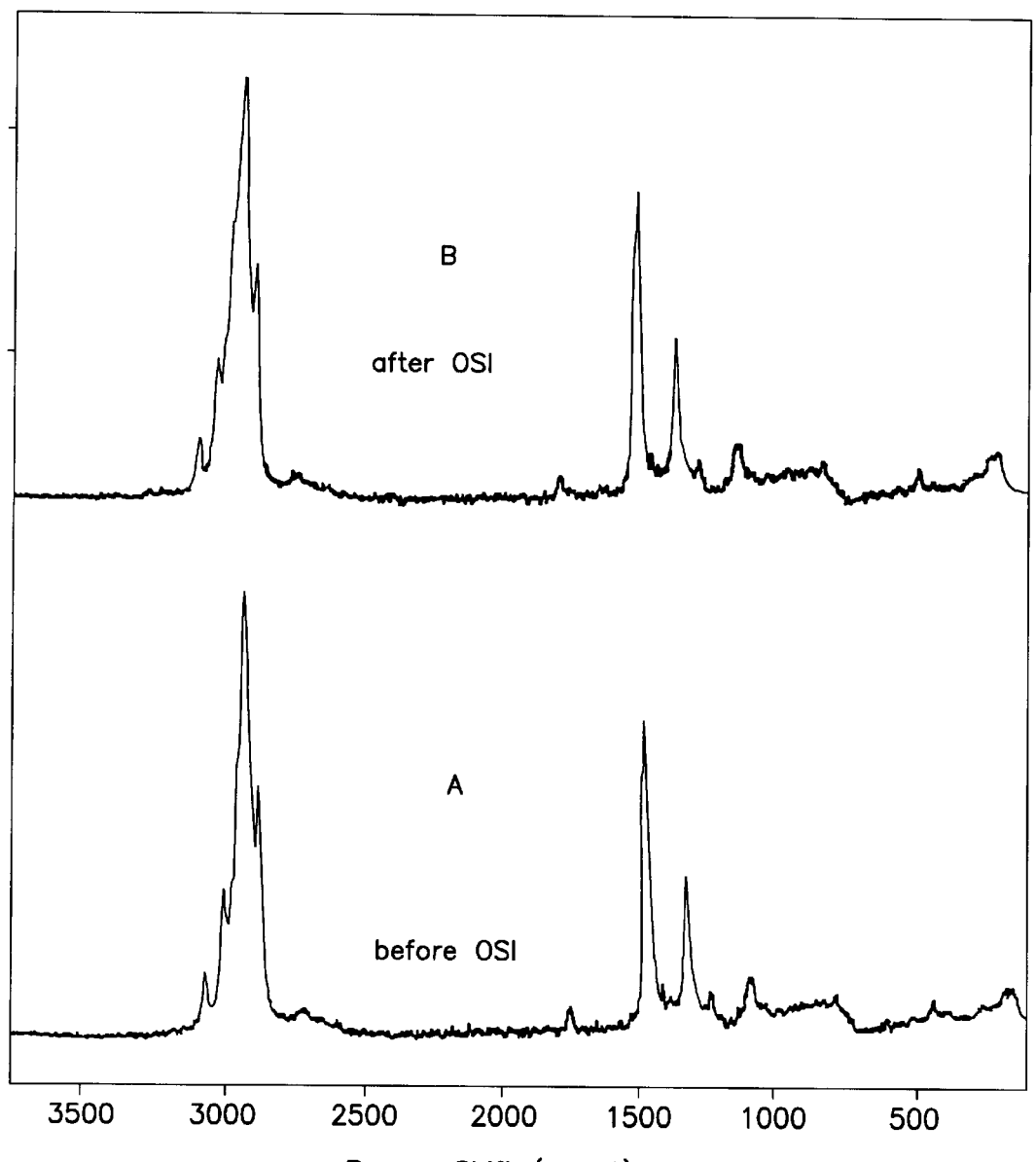
FIG. 4 shows Raman spectra of (A) untreated cyclopropanated trioleoylglycerol; and (B) cyclopropanated trioleoylglycerol after being treated by passing air through a 110° C. sample for 16.05 hours.

FIG. 3 shows the Raman spectra of untreated trioleoylglycerol (A) and trioleoylglycerol after being subjected to OSI (B). The spectra show substantial changes in the peaks at 1262, 1659 and 1747 cm$^{-1}$. In contrast, as shown in FIG. 4, the Raman spectra of untreated cyclopropanated trioleoylglycerol (A) and cyclopropanated trioleoylglycerol after being subjected to OSI (B) are essentially identical.

Figure 5:
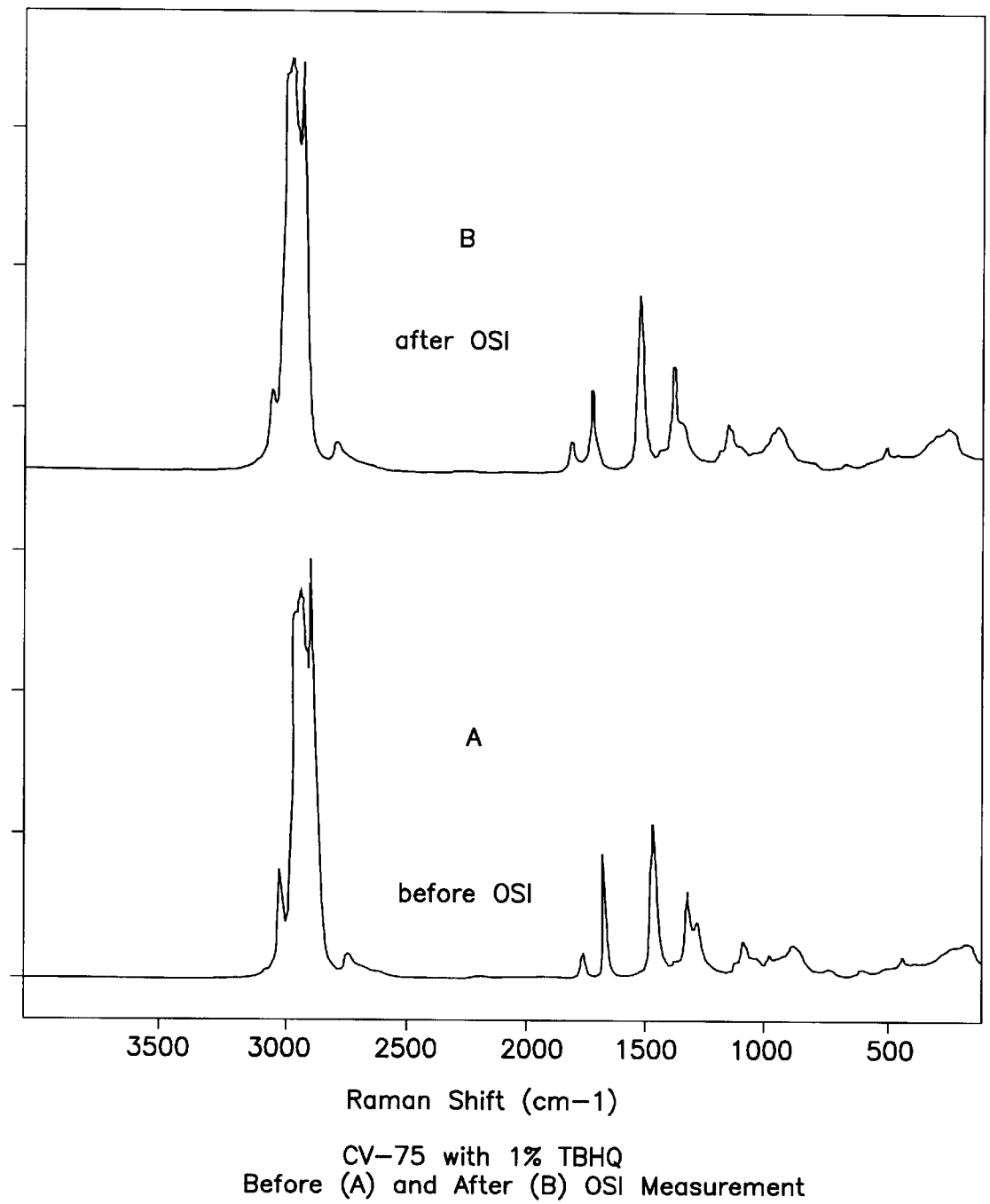
FIG. 5 shows Raman spectra of (A) untreated CV-75 with 1% t-butylhydroquinone ("TBHQ"); and (B) CV-75 with 1% TBHQ after being treated by passing air through a 110° C. sample for 150.4 hours.
Figure 6:
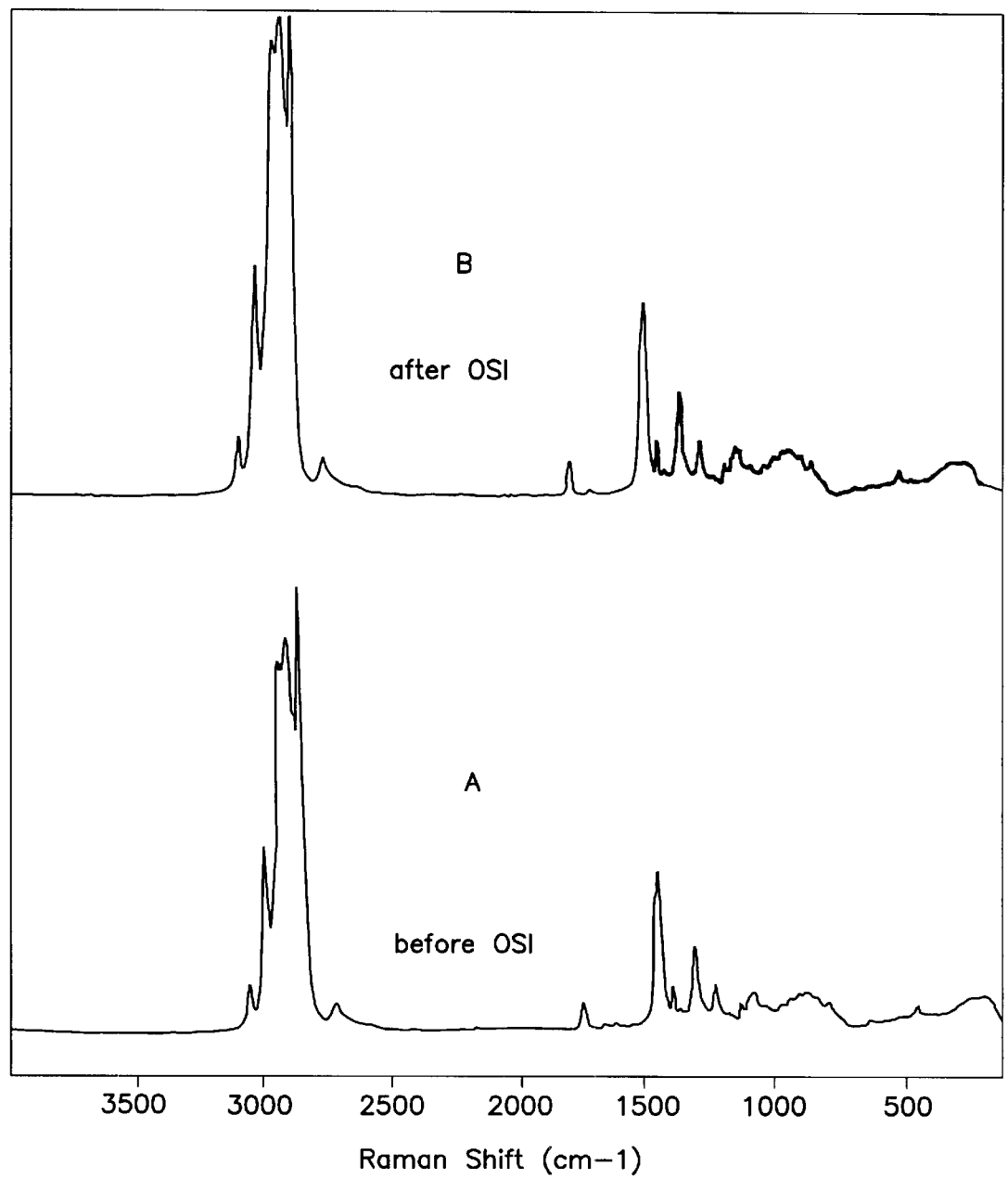
FIG. 6 shows Raman spectra of (A) untreated cyclopropanated CV-75 with 1% TBHQ; and (B) cyclopropanated CV-75 with 1% TBHQ after being treated by passing air through a 110° C. sample for 211.75 hours.
Figure 7:
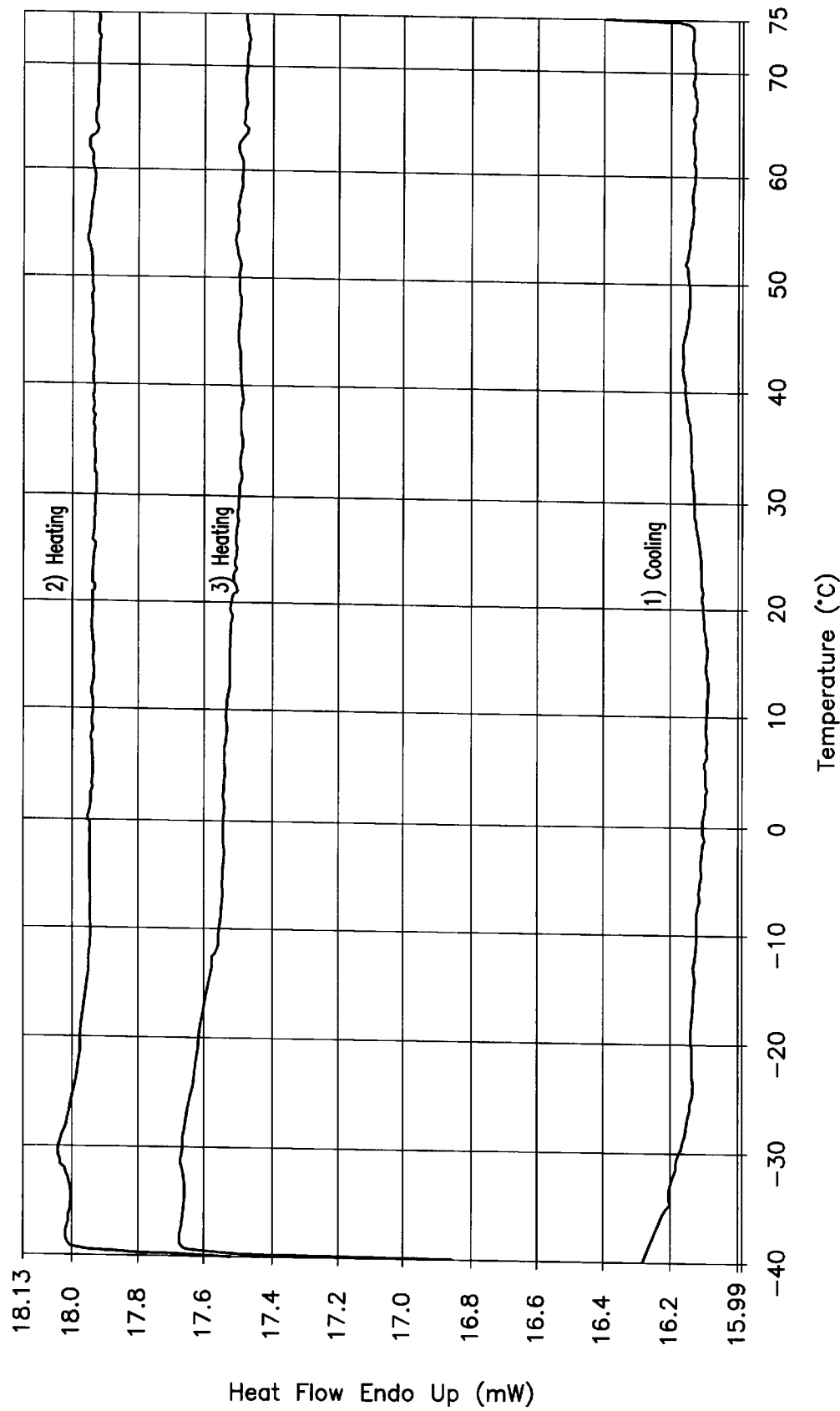
FIG. 7 shows a DSC trace observed from a sample of dichlorocyclopropanated CV-75 ("DCCP CV-75") while (a) loading the sample at 20° C. and holding for 10 minutes at that temperature, (b) heating the sample to 75° C. at 40.0° C./min, (c) holding the sample at 75° C. for 10 minutes, (d) cooling the sample from 75° C. to −40° C. at 1.00° C./min (shown in the Figure as "1) Cooling"), (e) holding the sample at −40° C. for 20 minutes, (f) reheating the sample to 75° C. at a rate of 1.00° C./min (shown as "3) Heating"), (g) again cooling the sample from 75° C. to −40° C. at 1.00° C./min, (h) holding the sample at −40° C. for 600 minutes, and (i) finally reheating the sample from −40° C. to 75° C. at a rate of 1.00° C./min (shown as "2) Heating").
Figure 8:
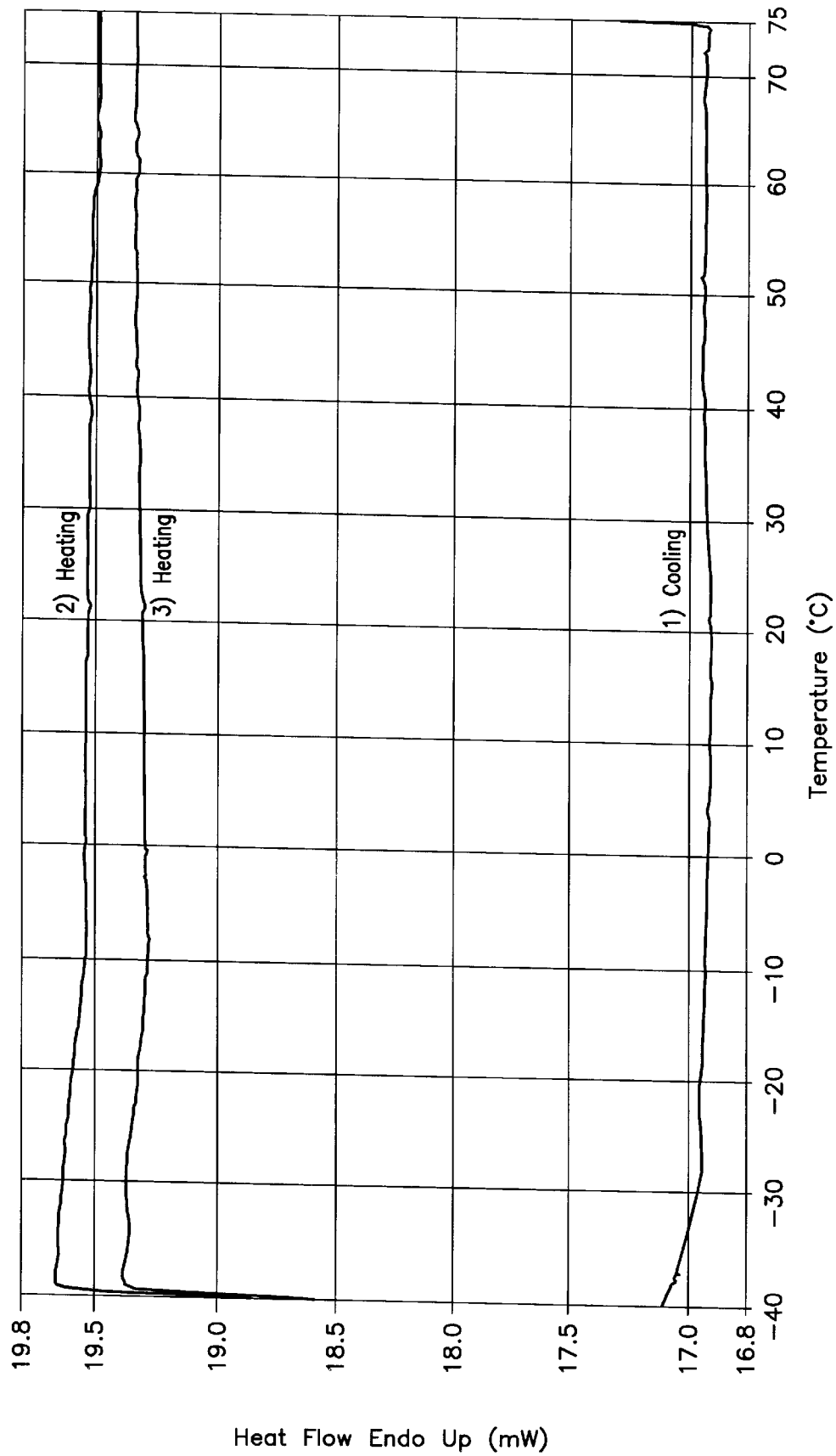
FIG. 8 shows a DSC trace observed from a sample of dichlorocyclopropanated trimethylolpropane ester of CV-75 fatty acid composition ("DCCP-TMP"). The DSC was measured while (a) loading the sample at 20° C. and holding the sample at 20° C. for 10 minutes at that temperature, (b) heating the sample to 75° C. at 40.0° C./min, (c) holding the sample at 75° C. for 10 minutes, (d) cooling the sample from 75° C. to −40° C. at 1.00° C./min (shown in the Figure as "1) Cooling"), (e) holding the sample at −40° C. for 20 minutes, (f) reheating the sample to 75° C. at a rate of 1.00° C./min (shown as "3) Heating"), (g) again cooling the sample from 75° C. to −40° C. at 1.00° C./min, (h) holding the sample at −40° C. for 600 minutes, and (i) finally reheating the sample from −40° C. to 75° C. at a rate of 1.00° C./min (shown as "2) Heating").
Figure 9:
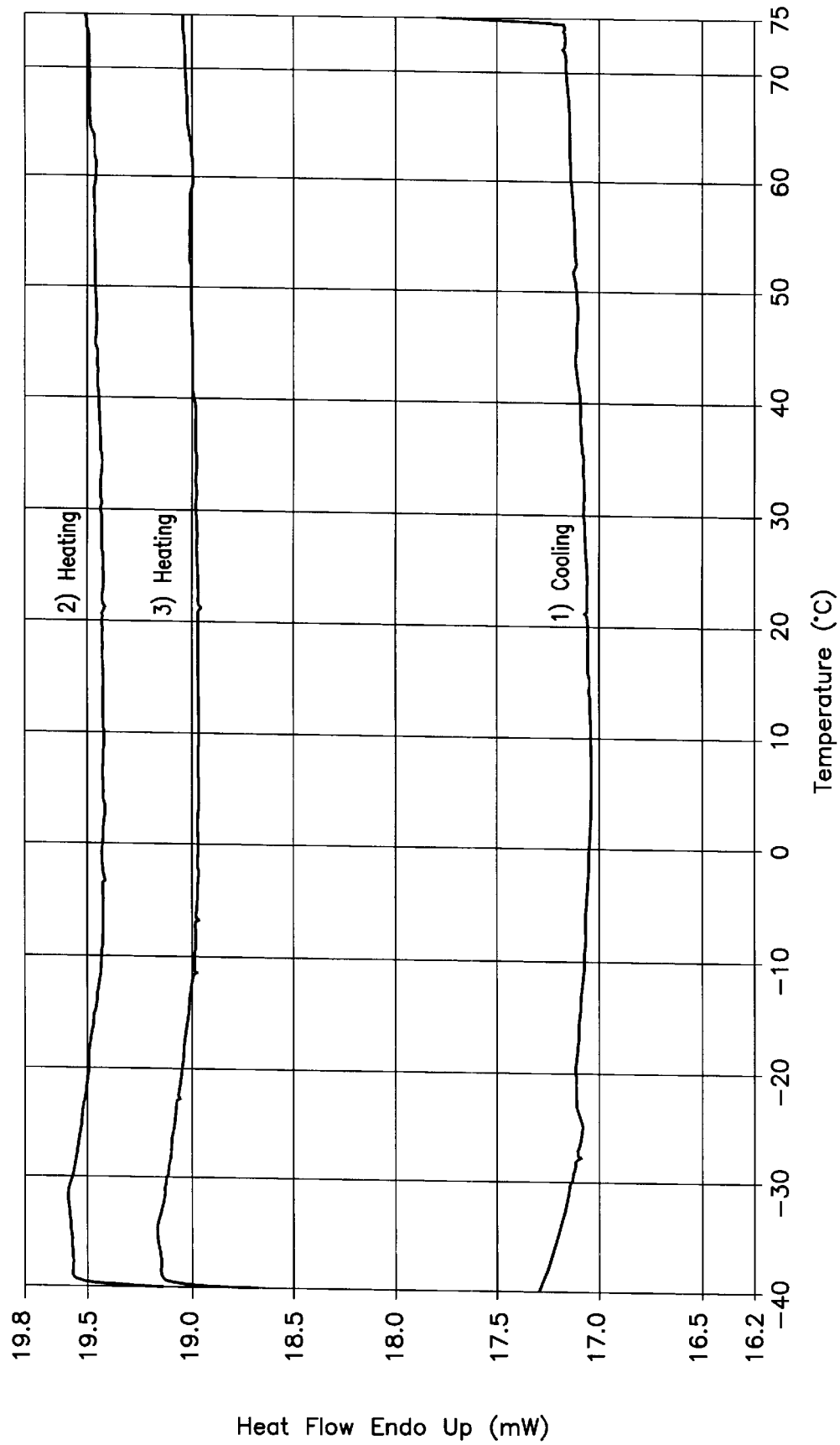
FIG. 9 shows a DSC trace observed from a sample of dichlorocyclopropanated neopentylglycol ester of CV-75 fatty acid composition ("DCCP-NPG"). The DSC was measured while (a) loading the sample at 20° C. and holding the sample at 20° C. for 10 minutes at that temperature, (b) heating the sample to 75° C. at 40.0° C./min, (c) holding the sample at 75° C. for 10 minutes, (d) cooling the sample from 75° C. to −40° C. at 1.00° C./min (shown in the Figure as "1) Cooling"), (e) holding the sample at −40° C. for 20 minutes, (f) reheating the sample to 75° C. at a rate of 1.00° C./min (shown as "3) Heating"), (g) again cooling the sample from 75° C. to −40° C. at 1.00° C./min, (h) holding the sample at −40° C. for 600 minutes, and (i) finally reheating the sample from −40° C. to 75° C. at a rate of 1.00° C./min (shown as "2) Heating").
Figure 10:
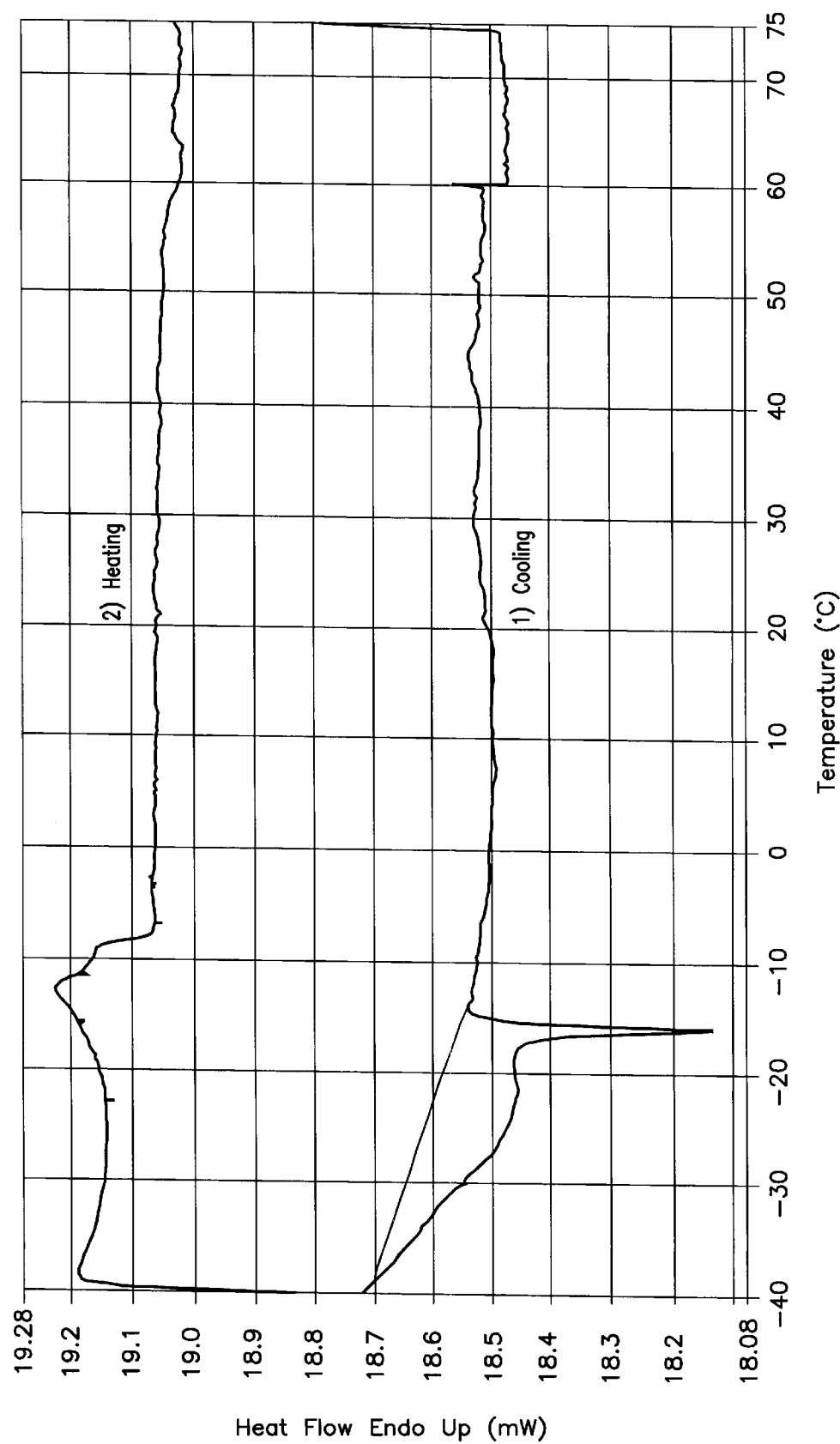
FIG. 10 shows a DSC trace observed from a sample of dichlorocyclopropanated methyl esters of CV-75 fatty acid composition ("DCCP-FAME"). The DSC was measured while (a) loading the sample at 20° C. and holding the sample at 20° C. for 10 minutes at that temperature, (b) heating the sample to 75° C. at 40.0° C./min, (c) holding the sample at 75° C. for 10 minutes, (d) cooling the sample from 75° C. to −40° C. at 1.00° C./min (shown in the Figure as "1) Cooling"), (e) holding the sample at −40° C. for 20 minutes, and (f) reheating the sample to 75° C. at a rate of 1.00° C./min (shown as "2) Heating").
Figure 11:
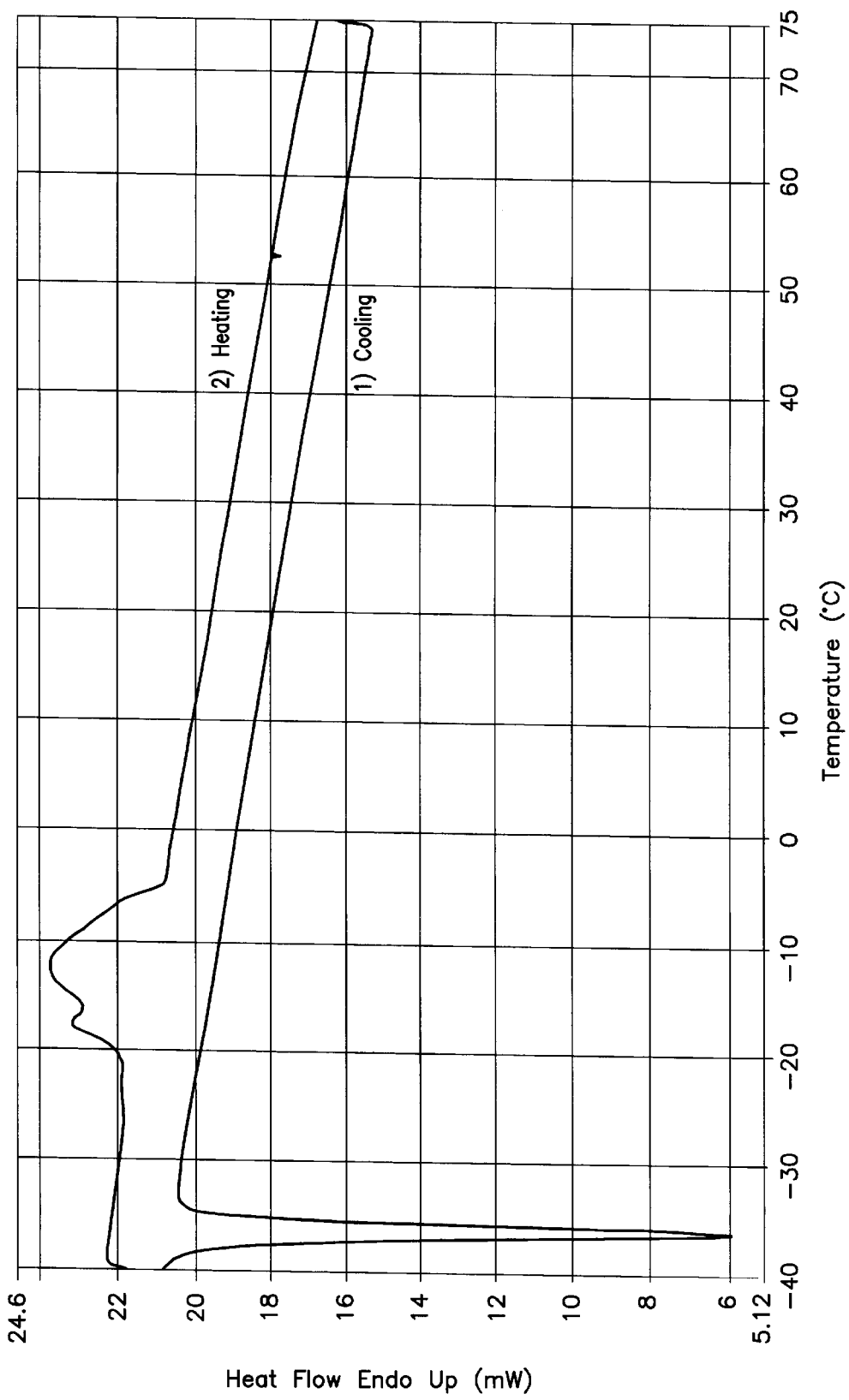
FIG. 11 shows a DSC trace observed from a sample of CV-75 fatty acid composition ("CV-75"). The DSC was measured while (a) holding the sample at 20° C. for 10 minutes, (b) heating the sample to 75° C. at 40.0° C./min, (c) holding the sample at 75° C. for 10 minutes, (d) cooling the sample from 75° C. to −40° C. at 1.00° C./min ("1) Cooling"), (e) holding the sample at −40° C. for 20 minutes, and (f) reheating the sample to 75° C. at a rate of 1.00° C./min ("2) Heating").
Figure 12:
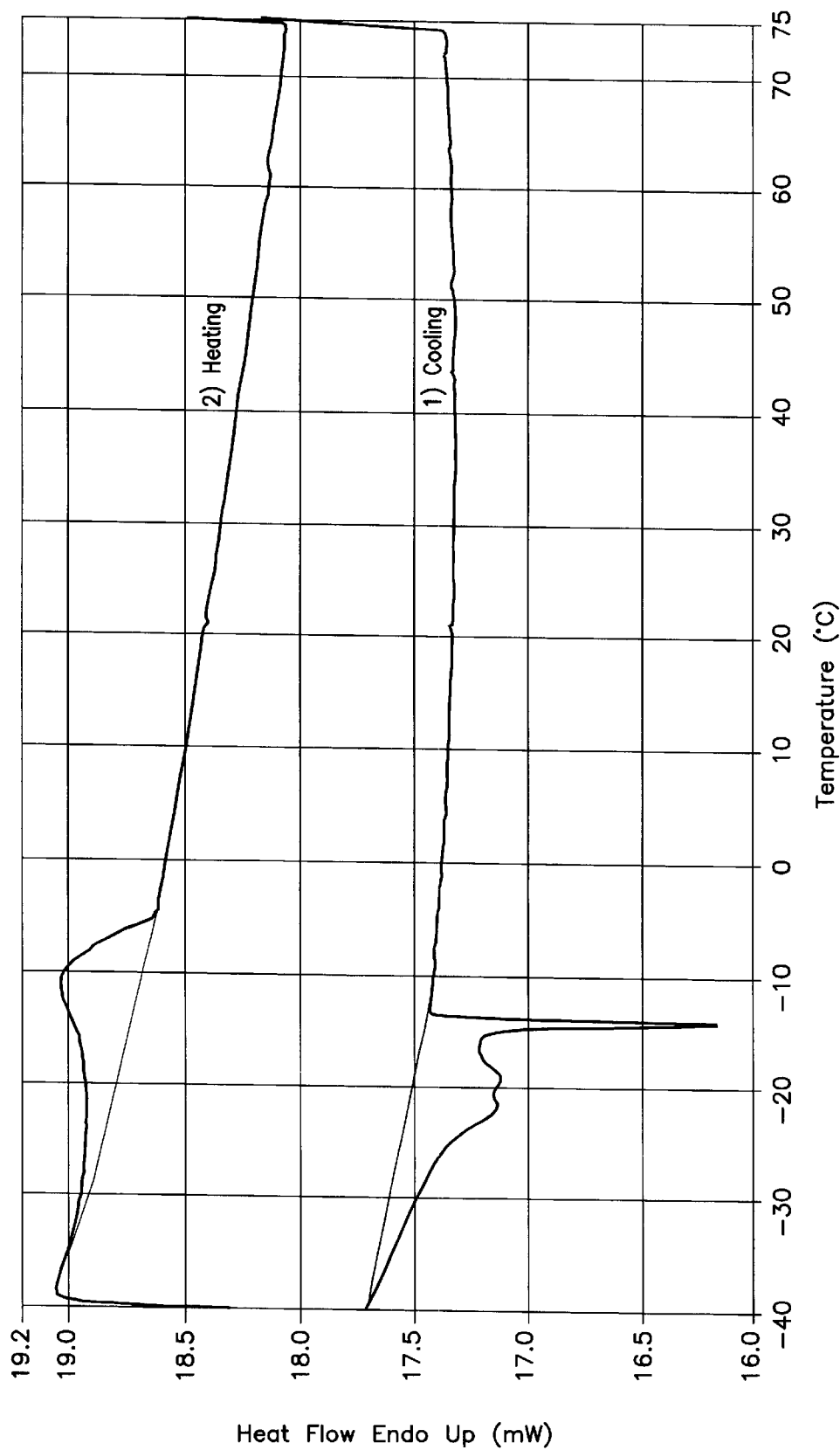
FIG. 12 shows a DSC trace observed from a sample of methyl esters of CV-75 fatty acid composition ("CV-75-FAME"). The DSC was measured while (a) holding the sample at 20° C. for 10 minutes, (b) heating the sample to 75° C. at 40.0° C./min, (c) holding the sample at 75° C. for 10 minutes, (d) cooling the sample from 75° C. to −40° C. at 1.00° C./min ("1) Cooling"), (e) holding the sample at −40° C. for 20 minutes, and (f) reheating the sample to 75° C. at a rate of 1.00° C./min ("2) Heating").

FIG. 5 shows the Raman spectra of untreated CV-75 with 1% TBHQ (A) and CV-75 with 1% TBHQ after being subjected to OSI (B). The spectra show substantial changes in the peaks at 1262, 1659 and 1747 cm$^{-1}$. In contrast, as shown in FIG. 6, the Raman spectra of untreated cyclopropanated CV-75 with 1% TBHQ (A) and cyclopropanated CV-75 with 1% TBHQ after being subjected to OSI (B) are essentially identical.

Example 5

Dichlorocyclopropanation of Unsaturated Fatty Acid Esters

Four different unsaturated fatty acid ester stocks were modified by cyclopropanation using chloroform and 50 wt. % aqueous sodium hydroxide. The starting unsaturated fatty acid ester stocks were CV-75 and three mixtures of esters formed by esterfication of the fatty acid mixture derived from hydrolysis of CV-75 with trimethylolpropane, neopentyl glycol and methanol respectively. CV-75 is a high oleic canola oil that contains about 85% triacylglycerols containing three unsaturated fatty acyl chains, mainly LOO (linoleic:oleic:oleic) and OOO (oleic:oleic:oleic). The triacylglycerol composition of CV-75 is shown in Table III below.

TABLE III

| Triacylglycerol Composition of CV-75 | | | | | | |
|---|---|---|---|---|---|---|
| LnOO | LOO | LOP | OOO | OOP | OOS | PSS |
| 7.36 | 19.16 | 1.87 | 58.66 | 5.86 | 2.48 | 0.09 |

CV-75 is shown in the first column.

**-P-palmitic; O-oleic; S-stearic; L-linoleic; Ln-Linolenic.

The following abbreviations are used to refer to the dichlorocyclopropanated products produced from reaction of the four unsaturated ester stocks with chloroform and 50 wt. % sodium hydroxide:

5A) DCCP-CV-75=Dichlorocyclopropanated CV-75;

5B) DCCP-TMP=Dichlorocyclopropanated trimethylolpropane esters of CV-75 Fatty Acids;

5C) DCCP-NPG=Dichlorocyclopropanated neopentyl glycol esters of CV-75 Fatty Acids;

5D) DCCP-FAME=Dichlorocyclopropanated methyl esters of CV-75 Fatty Acids.

The following procedure was used to produce dichlorocyclopropanated adducts of the four unsaturated ester stocks. To a stirred solution of 100 g of the unsaturated ester in 200 mL of chloroform containing 1.84 g of benzyltriethylammonium chloride was added dropwise a solution of 50 g of sodium hydroxide in 50 ml, of water. The resulting mixture was stirred at 50 to 60° C. for 5 h and then cooled to room temperature. The reaction mixture was diluted with 200 mL of hexane and the organic layer was separated from the aqueous layer using a separatory funnel. The aqueous layer was extracted with 100 mL of hexane and the combined organic extracts were washed with water (3×200 mL)

and dried over anhydrous sodium sulfate. The solvents were evaporated under vacuum to provide the desired product. The Iodine Values measured for the final products (shown below) indicated that essentially all of the carbon-carbon double bonds in the fatty acyl chains had been converted into dichlorocyclopropyl groups.

| | Iodine Values | |
|---|---|---|
| | CV-75: | 96.5 |
| 5A) | DCCP-CV-75: | 2.9 |
| 5B) | DCCP-TMP: | 2.2 |
| 5C) | DCCP-NPG: | 2.0 |
| 5D) | DCCP-FAME: | 1.6 |

NMR, Raman and FT-IR Spectral Data
DCCP-CV-75
$^1$H-NMR (300 MHz, CDCl$_3$) δ5.26 (m, 1H), 4.31–4.10 (m, 4H), 2.30 (t, 6H, J=7.5 Hz), 1.73–1.25 (m, 84H), 0.86 (t, 9H, J=6.6 Hz).
$^{13}$C-NMR (75.4 MHz, CDCl$_3$) δ173.1, 172.7, 68.9, 65.9, 62.1, 34.2, 34.0, 33.0, 32.9, 31.9, 31.5, 31.1, 29.7, 29.5, 29.4, 29.3, 29.1, 29.0, 28.7, 28.6, 24.9, 24.8, 22.7, 20.8, 20.7, 14.1.
Raman Shift (cm$^{-1}$) (neat): 3004, 2929, 2854, 1744, 1439, 1304, 1078, 836, 518, 210.
IR (cm$^{-1}$) (neat): 2960, 2923, 2854, 1739, 1464, 1149.
DCCP-TMP
$^1$H-NMR (300 MHz, CDCl$_3$) δ4.00 (s, 6H), 2.30 (t, 6H, J=7.5 Hz), 1.71–1.24 (m, 86H), 0.88 (t, 12H, J=7.5 Hz).
$^{13}$C-NMR (75.4 MHz, CDCl$_3$) δ173.3, 65.9, 63.6, 40.6, 34.6, 34.2, 34.0, 33.1, 33.0, 32.9, 31.9, 31.7, 31.5, 31.1, 29.7, 29.5, 29.4, 29.3, 29.1, 29.0, 28.7, 28.4, 24.9, 24.8, 23.0, 22.7, 22.5, 20.8, 20.7, 14.1, 14.0, 7.4.
Raman Shift (cm$^{-1}$) (neat): 3006, 2930, 2903, 2854, 1742, 1439, 1303, 1239, 1063, 841, 518, 274.
IR (cm$^{-1}$) (neat): 2922, 2854, 1737, 1464, 1240, 1150.
DCCP-NPG
$^1$H-NMR (300 MHz, CDCl$_3$) δ3.87 (s, 4H), 2.30 (t, 4H, J=7.5 Hz), 1.71–1.24 (m, 56H), 0.96 (s, 6H), 0.88 (t, 9H, J=6.6 Hz).
$^{13}$C-NMR (75.4 MHz, CDCl$_3$) δ173.4, 68.9, 65.9, 34.6, 34.2, 33.1, 33.0, 32.9, 32.8, 31.9, 31.8, 31.6, 31.5, 31.1, 29.7, 29.5, 29.4, 29.3, 29.2, 29.1, 29.0, 28.7, 28.6, 28.4, 24.9, 24.8, 22.7, 22.5, 21.8, 20.8, 20.7, 14.1, 14.0.
Raman Shift (cm$^{-1}$) (neat): 3007, 2928, 2854, 1739, 1439, 1303, 1240, 1077, 784, 519, 402, 273, 210.
IR (cm$^{-1}$) (neat): 2924, 2854, 1735, 1464, 1246, 1167.
DCCP-FAME
$^1$H-NMR (300 MHz, CDCl$_3$) δ3.65 (s, 3H), 2.30 (t, 2H, J=7.5 Hz), 1.67–1.19 (m, 28H), 0.87 (t, 3H, J=6.8 Hz).
$^{13}$C-NMR (75.4 MHz, CDCl$_3$) δ174.1, 65.9, 51.4, 34.0, 33.1, 31.5, 31.1, 29.7, 29.5, 29.4, 29.3, 29.1, 29.0, 28.7, 28.4, 24.8, 22.7, 20.7, 14.1.
Raman Shift (cm$^{-1}$) (neat): 3010, 2928, 2854, 1741, 1439, 1304, 1242, 1063, 843, 518, 274.
IR (cm$^-$) (neat): 2924, 2854, 1737, 1464, 1443, 1199, 1178.

Example 6

DSC of Dichlorocyclopropanated Adducts

DSC samples of the dichlorocyclopropanated adducts prepared in Example 5 were prepared and loaded at room temperature. Melting temperature (T$_m$) and ΔH were determined using the following sequence: a) hold the sample at 20° C. for 10 min; b) heat the sample from 20° C. to 75° C. at 40.0° C./min; c) hold the sample at 75° C. for 10 min; d) cool the sample from 75° C. to −40° C. at a rate of 1.00° C./min; e) hold the sample at −40° C. for 20.0 min; f) heat the sample from −40° C. to 75° C. at a rate of 1.00° C./min; g) cool the sample from 75° C. to −40° C. at 1.00° C./min; h) hold the sample at −40° C. for 600 min; i) heat the sample from −40° C. to 75° C. at 1.00° C./min. FIGS. 7–10 show the DSC curves obtained for DCCP-CV-75 (5A), DCCP-TMP (5B), DCCP-NPG (5C) and DCCP-FAME (5D) respectively. The results shown below demonstrate that dichlorocyclopropanation can produce modified vegetable oil having a very low melting point and enthalpy of melting.

| | |
|---|---|
| CV-75: | T$_m$ = −5° C.; ΔH = 67–77 J/g; T$_c$ = −36° C. |
| CV-75-FAME: | T$_m$ = −5° C.; ΔH = 9 J/g; T$_c$ = −14° C.. |
| DCCP-CV-75: | T$_m$ = <−40° C.; ΔH = 4.5 J/g. |
| DCCP-TMP: | T$_m$ = <−40° C.; ΔH = 0 J/g. |
| DCCP-NPG: | T$_m$ = −13° C.; ΔH = 5.1 J/g. |
| DCCP-FAME: | T$_m$ = −9° C.; ΔH = 3.5 J/g; T$_c$ = −16° C. |

Example 7

Viscosities of Dichlorocyclopropanated Adducts

The viscosities of the dichlorocyclopanated adducts prepared in Example 5 were determined at 40° C. and 100° C. using a Brookfield viscometer type R.V.F. at a 20 rpm setting and are listed in Table IV below.

TABLE IV

Viscosities of Dichlorocyclopropanated Adducts

| Ester Stock | Viscosity (cP) at 40° C. | Viscosity (cP) at 100° C. | Viscosity Index |
|---|---|---|---|
| CV-75 | 39.5 | 8.3 | 205 |
| DCCP-CV-75 | 182 | 21.5 | 138 |
| DCCP-TMP | 110 | 15 | 141 |
| DCCP-NPG | 51 | 8.8 | 152 |
| DCCP-FAME | 8.3 | 2.9 | 326 |

Example 8

Difluorocyclopropanation of a High Oleic Canola Oil

The following procedure was used to produce difluorocyclopropanated adducts of unsaturated fatty acid triglycerol esters. To a solution of 5.0 g of CV-75 in 5.0 mL of diglyme heated under reflux, a solution of 45 g of sodium chlorodifluoroacetate in 30 ml of diglyme was added dropwise. After the addition, the reaction mixture was heated under reflux for another 30 min before being cooled to room temperature. The cooled reaction mixture was diluted with 150 ml of hexane and washed with water (3×100 mL). The solvent was removed from the organic phase under vacuum and the product was purified by silica gel column chromatography (eluting with ethyl ether in hexane) to provide 5.0 g of the difluorocyclopropanated product (57% double bond conversion to difluorocyclopropyl groups based on Raman analysis).
$^{19}$F-NMR (282 MHz, CDCl$_3$) −134.73, −135.28, −164.41, −164.96.

Example 9

Cyclopropanation of a High Oleic Canola Oil

To a solution of 25 g of CV-75 in 50 mL of dry diethyl ether was added 16.5 mL of dibromomethane, 21 g of zinc powder, and 3.1 g of copper(I) chloride. The mixture was stirred under reflux while 0.51 mL of titanium(IV) chloride was added dropwise. The resulting mixture was heated under reflux for 2.5 h. Upon completion of the reaction, as indicated by a stopping of gas evolution, the contents of the reaction was transferred to another flask, cooled in ice, and treated while stirring with 75 mL of saturated aqueous ammonium chloride. The precipitates were removed by vacuum filtration and washed with hexane (2×50 mL). The aqueous layer of the filtrate is separated and extracted with hexane (2×50 mL), and the combined organic layers were washed with 100 mL of saturated aqueous sodium chloride solution and dried over anhydrous sodium sulfate. The solvents were removed using a rotary vacuum evaporator to provide 25 g of the cyclopropanated product.

This reaction is highly exothermic and therefore must be performed with caution.

Example 10

Preparation of Zn-Cu couple (III)

Zinc copper couple (III) was formed using the method described by LeGoff, *J. Org. Chem.* 29:2048–50 (1964). Basically, 35 g of zinc dust was added to a hot, rapidly stirred, solution of 2.0 g cupric acetate monohydrate in 50 mL of glacial acetic acid. After about 1 minute, all of the copper deposited on the zinc. The couple was allowed to settle for 1 minute, then the acetic acid was decanted. The dark reddish gray couple was then washed with 50 mL acetic acid and collected by vacuum filtration. After the couple was washed with ether (2×50 mL), it was ready to be used.

Example 11

Cyclopropanation of Unsaturated Fatty Acid Esters with: 1) dibromomethane and 2) zinc copper Couple Formed in Situ Using chlorotrimethylsilane and 1,2-dibromoethane as Activators Two drops of 1,2-dibromoethane and 0.5 mL chlorotrimethylsilane (TMSCl) were added to a suspension of zinc dust (10.4 g) and copper chloride (1.6 g) in dry ether (20 mL). The resulting mixture was stirred at room temperature for 15 minutes and then heated to reflux. A solution of CV-75 (12.0 g) and dibromomethane (8.4 mL) in dry ether (10 mL) was added dropwise and the resulting mixture was stirred under reflux for 8 hours. The reaction mixture was cooled to room temperature and treated, while stirring, with 50 mL of a saturated aqueous solution of ammonium chloride. The precipitates were removed by vacuum filtration and washed with hexane (2×50 mL). The aqueous layer of the filtrate was separated and extracted with hexane (2×50 mL), and the combined organic lyers were wahed with 50 mL of a saturated aqueous solution of sodium chloride and dried over anhydrous sodium sulfate. The solvents were removed at reduced pressure using a rotary evaporator to provide 12 g of the cyclopropanated product (>90% cyclopropanation as indicated by Raman analysis).

This reaction is slightly exothermic, milder than the reaction shown in Example 11. Advantageously, this reaction uses dibromomethane (which is relatively inexpensive and readily available) and does not require separate preparation of zinc-copper couple.

$^1$H-NMR (300 MHz, CDCl$_3$) δ5.26 (m, 1H), 4.31–4.10 (m, 4H), 2.30 (t, 6H, J=7.5 Hz), 1.28–1.25 (m, 78H), 0.86 (t, 9H, J=6.6 Hz), 0.63–0.51 (m, 10H), −0.33 to −0.37 (m, 2H).

$^{13}$C-NMR (75.4 MHz, CDCl$_3$) δ173.2, 172.8, 68.8, 62.1, 34.2, 34.0, 31.9, 30.2, 30.1, 29.7, 29.5, 29.4, 29.3, 29.1, 29.0, 28.7, 28.6, 24.9, 24.8, 22.7, 15.8, 15.7, 14.1, 10.9.

Raman Shift (cm$^{-1}$) (neat): 3066, 2994, 2932, 2896, 2855, 1747, 1442, 1396, 1298, 1215.

FT-IR (cm$^{1-}$) (neat): 3080, 3000, 2932, 1032.

Example 12

Physical Properties of Cyclopropanated Methyl and Polyol Esters of CV-75

Various physical properties of cyclopropanated methyl and polyol esters of CV-75 were evaluated. The Iodine value was determined using the Wijs method (A.O.C.S. Cd 1-25). The Viscosity at 40° C. and 100° C. was determined as described in Example 7. The viscosity index was determined by ASTM method D 2270. The melting temperature and melting enthalpy were determined as described in Example 3. The results are shown in Table V, below.

CV-75 is an untreated triacylglycerol. CP-CV-75 is a cyclopropanated triacylglycerol that can be formed by any of the methods described herein. CP-FAME is a Fatty Acid Methyl Ester (FAME) of CV-75, CP-NPG is a neopentyl glycol ester of CV-75 and CP-TMP is a trimethylolpropane ester of CV-75. The synthesis of CP-FAME, CP-NPG and CP-TMP are described below.

a. CP-FAME 10 grams of a 30% NaOMe in methanol was added to a solution of 2,014 grams of CV-75 in 5.545 mL of methanol. The resulting mixture was heated under reflux for 3 hours and then gradually cooled to room temperature. 1000 mL of water was added and methanol was removed by rotary evaporation. The aqueous phase was extracted with hexane (5×1000 mL) and the organic extracts were combined and concentrated by rotary evaporation. The product was purified through vacuum distillation to provide 1,800 grams of the methyl ester of CV-75.

b. CP-NPG and CP-TMP

A mixture of methyl ester of CV-75 (702 g) and the polyol (64.62 g or trimethylol propane or 104.15 g neopentyl glycol) was loaded into a vacuum distillation apparatus and heated at 70° C. to 80° C. under high vacuum until no more water was collected. The mixture was cooled to 60° C. and 5.0 g of 30% NaOMe in methanol was added. The mixture was heated to about 90° C. until no more methanol was collected in the receiver which was cooled at −78° C. The excess methyl ester was distilled off at about 180° C. The remaining product was decolorized using activated carbon to yield the polyol ester of CV-75.

TABLE V

Physical Properties of Cyclopropanated Methyl and Polyol Esters of CV-75

| | Iodine Value | Viscosity at 40° C. | Viscosity at 100° C. | Viscosity Index | Melting Temp (° C.) | Melting Enthalpy (j/g) |
| --- | --- | --- | --- | --- | --- | --- |
| CV-75 | 96 | 40 | 8.3 | 205 | −8 | 71 |
| CP-CV-75 | 10.6 | 103 | 15 | 156 | −7.8 | 7.8 |
| CP-FAME | 13.2 | 8.4 | 2.7 | 211 | −9.9 | 5.5 |
| CP-NPG | 7.3 | 13.8 | 2.7 | 280 | −23 | 5.1 |
| CP-TMP | 8.5 | 98 | 14.3 | 155 | <−40 | 0 |

The results in Table V show that the Iodine Values of the cylcopropanated product are substantially less than the untreated triacylglycerol. However, the melting temperature is as low or lower than the starting material.

Example 13

Figure 13:
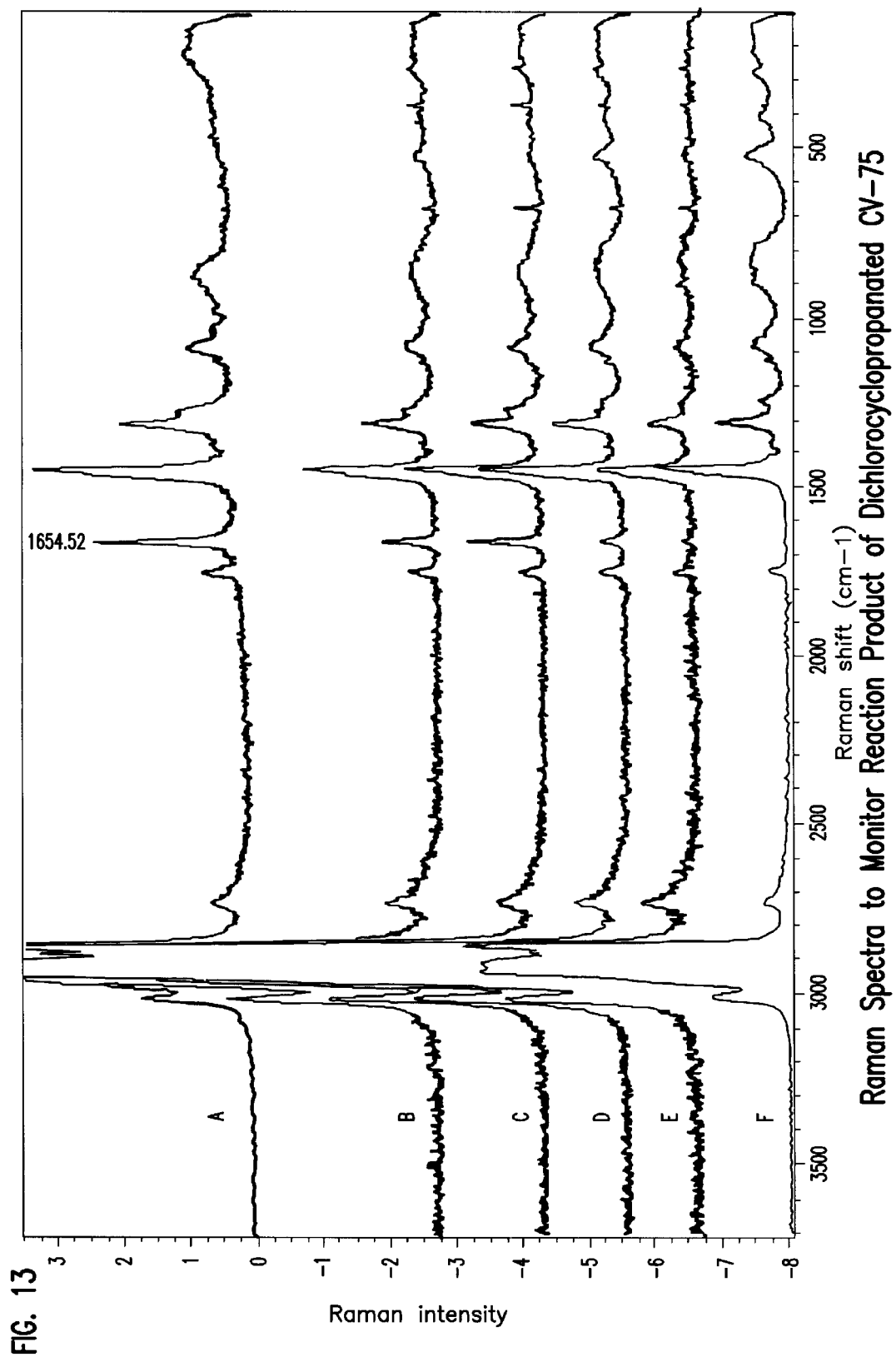
FIG. 13 shows Raman spectra of (A) untreated CV-75 ("CV-75"); (B) DCCP reaction end product using chloroform (7.5 molar equivalents per double bond), 50% NaOH (1.0 molar equivalents per double bond), and benzyltriethylammonium chloride (0.01 molar equivalents per double bond), 55° C., 6 h; (C) DCCP reaction end product using chloroform (7.5 molar equivalents per double bond), 50% NaOH (2.0 molar equivalents per double bond), and benzyltriethylammonium chloride (0.01 molar equivalents per double bond), 55° C., 6 h; (D) DCCP reaction end product using chloroform (7.5 molar equivalents per double bond), 50% NaOH (3.0 molar equivalents per double bond), and benzyltriethylammonium chloride (0.01 molar equivalents per double bond), 55° C., 6 h; (E) DCCP reaction end product using chloroform (7.5 molar equivalents per double bond), 50% NaOH (4.0 molar equivalents per double bond), and benzyltriethylammonium chloride (0.01 molar equivalents per double bond), 55° C., 6 h; and (F) DCCP reaction end product using chloroform (7.5 molar equivalents per double bond), 50% NaOH (7.5.0 molar equivalents per double bond), and benzyltriethylammonium chloride (0.01 molar equivalents per double bond), 55° C., 6 h.

Degree of dichlorocyclopropanation of CV-75 Using Different Amounts of 50% Aqueous NaOH Five unsaturated fatty acid ester stocks (CV-75) were modified by dichlorocyclopropanation using chloroform and varying amounts 50 wt % aqueous sodium hydroxide using the procedure described in Example 5. The results are shown in FIG. 13.

Spectrum A is CV-75, untreated triacylglycerol. Spectrum B is dochlorocyclopropanated CV-75 formed using chloroform (7.5 molar equivalents per double bond), 50% NaOH (1.0 molar equivalents per double bond), and benzyltriethylammonium chloride (0.01 molar equivalents per double bond), 55° C., 6 h. Spectra C, D, E and F are cyclopropanated CV-75 formed using the same reagents as Spectrum B, but with 2.0 molar equivalents per double bond 50% NaOH, 3.0 molar equivalents per double bond 50% NaOH, 4.0 molar equivalents per double bond 50% NaOH, and 7.5.0 molar equivalents per double bond 50% NaOH, respectively.

The peak at 1654.52 cm$^{-1}$ represents the carbon-carbon double bond absorption in the Raman Spectrum. In spectrum A, the untreated triacylglycerol, this peak is very pronounced. However, as the amount of 50% NaOH used in forming the dichlorocyclopropanated product is increased, the peak at 1654.52 cm$^{-1}$ decreases proportionately. Spectrum E, in which 4.0 equivalents 50% NaOH was added per double bond, shows virtually no peak at 1654.52 cm$^{-1}$. Spectrum F (7.5 molar equivalents per double bond) is completely dichlorocyclopropanated (e.g., no carbon-carbon double bonds).

Example 14

Dichlorocyclopropanation of Unsaturated Fatty Acid Esters Using Chloroform and Solid NaOH Catalyzed by Benzyltriethylammonium Chloride A solution of 18 g of CV-75 in 45 mL, chloroform containing 0.15 g of benzyltriethylammonium chloride was placed in a 500 mL round bottomed flask fitted with a magnetic stirrer and reflux condenser. 8.8 g of powdered sodium hydroxide was added to this solution. The resulting mixture was vigorously stirred. After 15 minutes, the mixture was cooled on an ice bath and filtered. The precipitates were washed with hexane (3×50 ml,) and the solvents from the combined filtrates were evaporated under vacuum to provide the product. The results are shown in FIG. 14.

Spectrum A is untreated triacylglycerol (CV-75). Spectrum B is dichlorocyclopropanated CV-75 formed by reacting CV-75 with chloroform (8.3 molar equivalents per double bond), solid NaOH (1.1 molar equivalents per double bond), and benzyltriethylammonium chloride (0.01 molar equivalents per double bond), at room temperature for 1 hour. Spectrum C is cyclopropanated CV-75 using chloroform (8.3 molar equivalents per double bond), solid NaOH (3.3 molar equivalents per double bond), and benzyltriethylammonium chloride (0.01 molar equivalents per double bond), at room temperature for 15 minutes. Spectrum D is dichlorocyclopropanated CV-75 using chloroform (7.5 molar equivalents per double bond), 50% NaOH (7.5.0 molar equivalents per double bond), and benzyltriethylammonium chloride (0.01 molar equivalents per double bond), at 55° C. for 6 hours (identical to FIG. 13(F)).

The peak at 1654.52 cm$^{-1}$ represents the carbon-carbon double bond absorption in the Raman Spectra. In spectrum A, the untreated triacylglycerol, this peak is very pronounced. However, as the amount of solid NaOH used in forming the dichlorocyclopropanated product is increased, the peak at 1654.52 decreases proportionately. Spectrum C, in which 3.3 equivalents of solid NaOH was added per double bond, shows virtually no peak at 1654.52 cm$^{-1}$. Spectrum D(7.5 molar equivalents per double bond) is completely dichlorocyclopropanated (e.g., no carbon-carbon double bonds).

Example 15

Oxidation Induction Time by Pressure Differential Scanning Calorimetry

Oxidation induction time (OIT) by measured by pressure differential scanning calorimeter (PDSC) can be used as an indication of a sample's oxidative stability. The OIT is the period of time during which the rate of oxidation of a sample accelerates from zero to a maximum. A longer period of time at a given temperature indicates a higher oxidative stability. The oxidation induction time was measured according to ASTM D-5483. The results are shown in Table VI, below.

The following samples were tested:

CV-75: untreated triacylglycerol

CP-CV-75: cyclopropanated triacylglycerol

CP-NPG: cyclopropanated neopentyl glycol ester of CV-75

DCCP-CV-75: dichlorocyclopropanated triacylglycerol

DCCP-NPG: dichlorocyclopropanated trimethylolpropane ester of CV-75

TABLE VI

| Oil | Oxidation Induction Time by PDSC, minutes | Temperature, ° C. |
| --- | --- | --- |
| CV-75 | 0.5 | 165 |
| CP-CV-75 | 1.5 | 180 |
| CP-NPG* | 12.5 | 155 |
| DCCP-CV-75* | 4.5 | 180 |
| DCCP-NPG* | 3.2 | 180 |

*contains 1% TBHQ and 50 ppm citric acid.

As shown in Table VI, the OIT values of the DCCP-CV-75 and DCCP-NPG indicate that these compounds are more stable than the cyclopropanated materials under the PDSC test conditions.

Thus, under current test conditions, the oxidative stability of the cyclopropanated triacylglycerol appears to be more stable than untreated CV-75. The required oxidative stability for a triacylglycerol greatly depends on its use, for example, the cyclopropanated triacylglycerols of the invention are well suited for use as hydraulic fluids.

Example 16

Gear Oil Scuff Test

The Gear Oil Scuff Test (GOST) was performed as described by Lacey, *Southwest Research Institute,* May 27, 1997. This test is used as a measure of boundary lubricating quality. During the GOST procedure, applied load on sliding wear test specimens is increased until lubrication failure occurs (evidenced by scuffing). The higher the load (in terms of grams) the better the boundary lubricating quality of the oil being tested.

TABLE VII

Gear Oil Scuff Test

| Oil | Scuff, grams | Viscosity at 100° C., cSt | Predicted Ryder | Predicted FZG |
|---|---|---|---|---|
| CP-CV-75* | 7375 | 13.16 | 4,014 | 10.4 |
| CP-NPG* | 6250 | 7.30 | 3,025 | 8.9 |
| DCCP-CV-75* | 12,000** | 17.87 | 5,663 | 13.0 |
| DCCP-NPG* | 12,000** | 13.18 | 5,290 | 12.6 |

*contains 1% TBHQ and 50 ppm citric acid.
**Sample did not scuff at 12,000 grams, the limit of the test.

As shown in Table VII both dichlorocyclopropanated oils showed excellent load capacities in the GOST test, exceeding the 12,000 gram load limit of the test. The data in Table VII indicate that the dichlorocyclopropanated oils are excellent extreme pressure lubricants. High load capacity can also be viewed as high boundary lubricating quality.

Example 17

Four Ball Wear Test

Four ball wear test (ASTM D-4172) is used to determine the relative wear preventive properties of lubricating fluids in sliding contact under the prescribed test conditions. Three 12.7-mm diameter balls are clamped together and covered with the lubricant to be evaluated and a fourth ball (the top ball) is pressed with force into the cavity formed by the three clamped balls for three-point contact. The temperature of the test lubricant is regulated and the top ball is rotated at 1200 rpm for 60 min. Lubricants are compared by using the average size of the scar diameters worn on the three lower clamped balls. The accepted scar diameter for lubrication greatly depends on the type of application. For example, the scar diameter of mineral oil based products for crankcase application is around 1.0 and for automatic transmission fluids (ATF) is between 0.4 to 0.6. The scar diameter in the four ball wear test can be managed through formulation to meet different application requirements. Both our cyclopropanated and dichlorocyclopropanated materials showed acceptable results (Table VIII).

TABLE VIII

Four Ball Wear Test

| Oil | Average Scar Diameter, mm | Test Temperature (° C.) | Test Duration (hrs) | Spindle Speed (rpm) | Load (kg) |
|---|---|---|---|---|---|
| CP-CV-75* | 0.86 | 75 | 1 | 1200 | 40 |
| CP-NPG* | 0.89 | 75 | 1 | 1200 | 40 |
| DCCP-CV-75* | 0.95 | 75 | 1 | 1200 | 40 |
| DCCP-NPG* | 0.84 | 75 | 1 | 1200 | 40 |

*contains 1% TBHQ and 50 ppm citric acid.

Example 18

Rust Protection Test

The rust protection test (ASTM D-1748) is used to evaluate the rust preventive properties of metal preservatives under conditions of high humidity. CP-CV-75 and CP-NPG showed excellent rust inhibition properties. Formulated mineral oil based lubricants normally have rust protection hours ranging from 70 to 720 hours at 49° C. Our cyclopropanated materials did not lose their rust protection properties even after 360 hours of test (the test was stopped at 360 hours). The rust protection test results for the two dichlorocyclopropanated compounds are not as good as their cyclopropanated counterparts.

TABLE IX

Rust Protection Test Results Using Polished Panels

| Oil | Rating | Temperature (° C.) | Duration (hrs) | # of Panels Used | # of Panels Passed |
|---|---|---|---|---|---|
| CP-CV-75* | Pass | 49 | 360 | 3 | 3 |
| CP-NPG* | Pass | 49 | 360 | 3 | 3 |
| DCCP-CV-75* | Fail | 49 | 24 | 3 | 0 |
| DCCP-NPG* | Fail | 49 | 96 | 3 | 0 |

*contains 1% TBHQ and 50 ppm citric acid.

The results in Table IX indicate that the dichlorocyclopropanated products do not offer rust protection, although these compounds do not cause corrosion. Therefore, these compounds perform well when combined with a rust protection agent. The cyclopropanated products offer rust protection.

Example 19

Corrosiveness and Oxidation Stability Test

The corrosiveness and oxidation stability test (ASTM D-4683) is performed by placing a large glass tube containing a sample of oil and metal specimens in a constant temperature bath and heating the sample for the specified number of hours while air is passed through the oil to provide agitation and source of oxygen. It simulates the environment encountered by fully formulated lubricating fluids in actual service. The use of metals provides catalytic reactive surfaces of those materials commonly found in real systems. The high temperature and air agitation help accelerate the oxidation reactions that are expected to occur. Moisture in the air also adds another realistic condition that promotes the oil breakdown by facilitating acid formation. Corrosiveness of the oil is determined by weight change and corroded appearance of the metals. Oxidative stability is determined by the following measurable effects: weight loss of oil due to evaporation; change of viscosity; increase in acid number; and measurable reaction products in the form of sludge.

TABLE X

Corrosiveness and Oxidation Stability (150° C., 96 Hours)

| | CP-CV-75* | CP-NPG* | DCCP-CV-75* | DCCP-NPG* |
|---|---|---|---|---|
| Metal Weight Change: | 3.67 | 8.02 | 14.20 | 12.85 |
| Copper, mg/cm$^2$ | 2.14 | −7.17 | −0.37 | 2.49 |
| Steel, mg/cm$^2$ | −0.01 | 0.00 | 0.38 | 3.10 |
| Aluminum, mg/cm$^2$ | −0.01 | 0.01 | 0.00 | −0.02 |
| Magnesium, mg/cm$^2$ | −0.11 | −0.05 | 4.95 | 3.39 |
| Cadmium, mg/cm$^2$ | 11.49 | 29.22 | 0.16 | 0.00 |
| Viscosity @ 40° C. (Initial), cSt | 77.86 | 31.08 | 134.20 | 103.70 |
| Viscosity @ 40° C. (Final), cSt | 115.60 | 71.29 | n/a | n/a |
| Viscosity Change @ 40° C., % | 48.47 | 129.38 | n/a | n/a |
| Viscosity @ 100° C. (Initial), cSt | 12.57 | 6.97 | 16.70 | 13.16 |
| Viscosity @ 100° C. (Final), cSt | 16.41 | 11.77 | n/a | n/a |
| Viscosity Change @ 100° C., % | 30.55 | 68.87 | n/a | n/a |
| Acid Number (Initial), mg KOH/g | 0.07 | 0.11 | <0.05 | 0.09 |

TABLE X-continued

Corrosiveness and Oxidation Stability (150° C., 96 Hours)

|  | CP-CV-75* | CP-NPG* | DCCP-CV-75* | DCCP-NPG* |
| --- | --- | --- | --- | --- |
| Acid Number (Final), mg KOH/g | 1.49 | 2.72 | n/a | n/a |
| Acid Number Change, mg KOH/g | 1.42 | 2.61 | n/a | n/a |
| Sludge, % volume | <0.05 | <0.05 | n/a | n/a |

Both the cyclopropanated and dichlorocyclopropanated oils were tested and provided acceptable results.

Example 20

Dry TOST Test

The oxidative stability of CV-75 and its cyclopropanated counterpart was compared directly using the dry TOST test and the results are summarized in Table XI.

TABLE XI

Dry Tost Test Results From SWRI

|  | CV-75 | CP-CV-75 |
| --- | --- | --- |
| ASTM D-043M Oxidation Characteristic* | | |
| Oxidation Lifetime, hours | ** | 519** |
| ASTM D-664 Acid Number | | |
| 336 Hours, mg KOH/g | ** | — |
| 500 Hours, mg KOH/g | — | — |
| ASTM D-664 Acid Number | | |
| 500 Hours, mg KOH/g | — | 0.66 |
| 668 Hours, mg KOH/g | — | 11.74 |

*Testing without water, sample every 168 hours (after the first 500 hours) up to 2,000 hours.
**Testing was stopped at 336 hours due to sample crystallization.
***Calculated hours to acid number = 2.0 mg KOH/g (should be less than this to keep the test going)
Mineral oils without inhibitors give oxidation lifetime less than 500 hours.

Based on the results shown in Table XI, the oxidation lifetime of cyclopropanated CV-75 is 519 hours. The oxidation lifetime of CV-75 could not be determined in this test due to the formation of crystallized materials after only 336 hours of test. The crystallized materials are polymers formed from the oxidative breakdown of the oil. This result again proves that the cyclopropanation technology is very effective in improving the oxidative stability of unsaturated vegetable oils. It should be noted that mineral oils without inhibitors generally give oxidation lifetime less than 500 hours.

The invention has been described with reference to various specific and preferred embodiments and techniques. The invention is not to be construed, however, as limited to the specific embodiments disclosed in the specification. It should be understood that many variations and modifications may be made while remaining within the spirit and scope of the invention.

What is claimed is:

1. A process for modifying an unsaturated polyol fatty acid ester stock comprising:
reacting the unsaturated polyol fatty acid ester stock with cyclopropanating agent to form a cyclopropanated product comprising polyol fatty acid ester which has at least one fatty acyl chain including at least one cyclopropyl group.

2. The process of claim 1 wherein the cyclopropanated product has an $OV_{50}$ value which is at least about 50% higher than that of the unsaturated polyol fatty acid ester stock.

3. The process of claim 1 comprising reacting the unsaturated polyol fatty acid ester stock with a sufficient amount of cyclopropanating agent to form a cyclopropanated product having an average cyclopropyl content of at least about 0.25.

4. The process of claim 1 comprising reacting the unsaturated polyol fatty acid ester stock with cyclopropanating agent which includes R'CHXY, wherein X is bromo, or iodo, Y is chloro, bromo or iodo, and R' is hydrogen or n-alkyl.

5. The process of claim 4 wherein the cyclopropanating agent further comprises zinc reagent.

6. The process of claim 5 wherein R'CHXY is $CH_2Br_2$ or $CH_2I_2$.

7. The process of claim 1 comprising reacting the unsaturated polyol fatty acid ester stock with cyclopropanating agent which is capable of adding $:CR^2R^3$ to a carbon-carbon double bond to form a cyclopropyl group, wherein $R^2$ is H, halo, alkyl, phenyl or substituted phenyl, and $R^3$ is H, halo or alkyl.

8. The process of claim 7 wherein the cyclopropanating agent which is capable of adding $:CH_2$, $:CF_2$,: $CCl_2$, $:CBr_2$, $Cl_2$ or a mixture thereof to the carbon-carbon double bond.

9. The process of claim 1 wherein the cyclopropanated product has an active methylene content at least about 10% lower than that of the unsaturated polyol fatty acid ester stock.

10. The process of claim 1 comprising reacting the unsaturated polyol fatty acid ester stock with sufficient cyclopropanating agent to form a cyclopropanated product having an OVI of at least about 50 hours.

11. The process of claim 1 wherein the cyclopropanated product has an enthalpy of melting which is at least about 10 J/g lower than that of the unsaturated polyol fatty acid ester stock.

12. The process of claim 1 wherein the cyclopropanating agent includes haloform and base.

13. The process of claim 12 wherein the haloform includes chloroform, bromoform, iodoform or a mixture thereof.

14. The process of claim 12 wherein the base includes alkali metal alkoxide, alkali metal hydroxide, alkaline earth hydroxide or alkali metal hydride.

15. The process of claim 12 wherein the base is an aqueous solution.

16. The process of claim 15 wherein the base is an aqueous solution of sodium hydroxide.

17. The process of claim 12 wherein the base is a solid.

18. The process of claim 17 wherein the solid base is a powder or a crystal.

19. The process of claim 17 wherein the base is solid sodium hydroxide.

20. The process of claim 12 comprising reacting the unsaturated polyol fatty acid ester stock with the haloform and the base in the presence of phase transfer catalyst to form the cyclopropanated product.

21. The process of claim 1 wherein the cyclopropanating agent includes trihaloacetate salt.

22. The process of claim 1 wherein the trihaloacetate salt includes alkali metal salt of trichloroacetic acid, dichlorofluoroacetic acid, chlorodifluoroacetic acid or a mixture thereof.

23. The process of claim 1 wherein the cyclopropanating agent includes dibromomethane and zinc copper couple wherein the zinc copper couples is formed in situ by contact with halotrialkylsilane and dihaloethane.

24. The process of claim 23 wherein halotrialkylsilane is chlorotrimethylsilane and dihaloethane is dibromoethane.

25. A lubricant comprising polyol fatty acid ester stock that includes polyol fatty acid ester having at least one fatty acyl chain including at least one cyclopropyl group.

26. The lubricant of claim 25 having an OVI of at least about 50 hours.

27. The lubricant of claim 25 having an Iodine Value of no more than about 50.

28. The lubricant of claim 25 having an active methylene content of no more than about 0.1.

29. The lubricant of claim 25 having an average unsaturation content of no more than about 0.5.

30. The lubricant of claim 25 comprising polyol fatty acid ester which includes at least one fatty acyl chain having at least one dihalocyclopropyl group.

31. The lubricant of claim 30 wherein the dihalocyclopropyl group is a dibromocyclopropyl group, a dichlorocyclopropyl group or a mixture thereof.

32. The lubricant of claim 30 wherein the dihalocyclopropyl group is a difluorocyclopropyl group.

33. A method for producing a lubricant comprising:
reacting an unsaturated polyol fatty acid ester stock with cyclopropanating agent to form a cyclopropanated product including polyol fatty acid ester which has at least one fatty acyl chain including at least one cyclopropyl group.

34. The method of claim 33 further comprising blending the cyclopropanated product with petroleum-based lubricant base stock to form a modified lubricant.

35. The method of claim 34 wherein the cyclopropanated product comprises about 0.1 wt % to about 20 wt % of the modified lubricant.

36. The method of claim 34 wherein the cyclopropanated product comprises about 1 wt % to about 5 wt % of the modified lubricant.

37. A polyol fatty acid ester stock which includes fatty acid ester including at least one fatty acyl chain having at least one cyclopropyl group; wherein said polyol fatty acid ester stock has an average cyclopropyl content of at least about 0.4 and a pour point of no more than about 0° C.

38. A polyol fatty acid ester comprising at least one fatty acyl chain which includes at least one dihalocyclopropyl group, wherein said polyol fatty acid ester has an average cyclopropyl content of at least about 0.25.

39. The polyol fatty acid ester of claim 38 including at least one fatty acyl chain which includes at least one dichlorocyclopropyl group.

40. The polyol fatty acid ester of claim 38 comprising fatty acid ester of a polyol selected from the group consisting of glycerol, ethylene glycol, diethylene glycol, triethylene glycol, neopentylglycol, pentaerythritol, trimethylolethane, trimethylolpropane, sorbitol, cyclohexanediol, inositol, glucose, galactose, sorbose and mixtures thereof.

41. An emulsifiable lubricant fluid comprising fatty acid salt stock comprising fatty acid salt having a fatty acyl chain which includes at least one cyclopropyl group.

42. The emulsifiable lubricant fluid of claim 41 wherein said fatty acid salt stock has an average cyclopropyl content of at least about 0.25.

43. The emulsifiable lubricant fluid of claim 41 wherein the fatty acyl chain has 10 to 24 carbon atom.

44. The emulsifiable lubricant fluid of claim 41 wherein the fatty acyl chain includes at least one dichlorocyclopropyl group.

45. The emulsifiable lubricant fluid of claim 41 wherein the fatty acid salt includes one or a mixture of fatty acid salts with acyl chains having 16 to 22 carbon atoms.

46. The emulsifiable lubricant fluid of claim 41 wherein the fatty acid salt includes fatty acid alkali metal salt.

47. The emulsifiable lubricant fluid of claim 41 wherein said emulsifiable lubricant fluid is a metal working fluid.

48. A lubricant comprising fatty acid monoester stock that includes fatty acid monoester having a fatty acyl chain including at least one cyclopropyl group.

49. A method of activating zinc copper couple comprising:
contacting zinc and copper halide with halotrialkylsilane and dihaloethane.

50. The method of claim 49 wherein halotrialkylsilane is chlorotrimethylsilane.

51. The method of claim 50 wherein dihaloethane is 1,2-dibromoethane.

52. The method of claim 50 wherein copper halide is copper(I)halide.

* * * * *